United States Patent
Hansen, Jr. et al.

(10) Patent No.: US 6,586,471 B1
(45) Date of Patent: Jul. 1, 2003

(54) HALOGENATED 2-AMINO-3, 4 HEPTENOIC ACID DERIVATIVES USEFUL AS NITRIC OXIDE SYNTHASE INHIBITORS

(75) Inventors: Donald W. Hansen, Jr., Skokie, IL (US); Barnett S. Pitzele, Skokie, IL (US); Ronald Keith Webber, St. Charles, MO (US); Mihaly V. Toth, St. Louis, MO (US); Pamela T. Manning, Labadie, MO (US); Alok K. Awasthi, Skokie, IL (US); Mahima Trivedi, Glenview, IL (US)

(73) Assignee: G. D. Searle, Chicago, IL (US)

( * ) Notice: Subject to any disclaimer, the term of this patent is extended or adjusted under 35 U.S.C. 154(b) by 0 days.

(21) Appl. No.: 09/835,193

(22) Filed: Apr. 13, 2001

Related U.S. Application Data

(60) Provisional application No. 60/197,027, filed on Apr. 13, 2000.

(51) Int. Cl.$^7$ ................. A61K 31/22; C07D 207/34; C07C 257/02; A61P 43/00
(52) U.S. Cl. ................. 514/557; 514/631; 564/225; 562/507; 548/486
(58) Field of Search .................. 514/557, 631; 564/225; 562/507; 548/486

(56) References Cited

U.S. PATENT DOCUMENTS

| | | | |
|---|---|---|---|
| 5,132,453 A | 7/1992 | Griffith | 562/560 |
| 5,684,008 A | 11/1997 | Hallinan et al. | 514/256 |
| 5,830,917 A | 11/1998 | Moore et al. | 514/634 |
| 5,854,251 A | 12/1998 | Hallinan et al. | 514/256 |
| 5,863,931 A | 1/1999 | Beams et al. | 514/357 |
| 5,919,787 A | 7/1999 | Hallinan et al. | 514/256 |
| 5,945,408 A | 8/1999 | Webber et al. | 514/63 |
| 5,981,511 A | 11/1999 | Gapud et al. | 514/63 |
| 5,994,391 A | 11/1999 | Lee et al. | 514/431 |
| 6,169,089 B1 | 1/2001 | Hallinan et al. | 514/256 |

FOREIGN PATENT DOCUMENTS

| | | | |
|---|---|---|---|
| EP | 0446699 | 5/2000 | C07K/5/06 |
| EP | 0521471 | 10/2000 | C07D/239/42 |
| WO | WO 9313055 | 7/1993 | C07C/257/14 |
| WO | WO 9316055 | 8/1993 | C07D/281/10 |
| WO | WO 9412165 | 6/1994 | A61K/31/155 |
| WO | WO 9414780 | 7/1994 | C07D/239/48 |
| WO | WO 9511014 | 4/1995 | A61K/31/00 |
| WO | WO 9511231 | 4/1995 | C07D/207/22 |
| WO | WO 9525382 | 9/1995 | H03H/17/02 |
| WO | WO 9525717 | 9/1995 | C07C/257/14 |
| WO | WO 9615120 | 5/1996 | C07D/257/06 |
| WO | WO 9633175 | 10/1996 | C07D/223/12 |
| WO | WO 9635677 | 11/1996 | C07D/223/12 |
| WO | WO 9706802 | 2/1997 | A61K/31/495 |
| WO | WO 9929865 | 6/1999 | C12N/15/28 |
| WO | WO 9946240 | 9/1999 | C07C/257/14 |

OTHER PUBLICATIONS

S. Moncada and E. Higgs, *Molecular Mechanisms and Therapeutic Strategies Related to Nitric Oxide* 1995, FASEB J., 9, 1319–1330.
S. Rozen, I. Shahak, and E. Bergmann, *Organic Fluorine Compounds Part XLIV. Preparation and Reactions of Epifluorohydrin* 1971, Synthesis 646–7.
E. Bergmann, S. Cohen, and I. Shahak, *Organic Fluorine Compounds. Part XX. Some Reactions of 1–Chloro–3–fluoropropan–2–ol and Epifluorohydrin* 1961, J Chem Soc 3448–52.
A. Jeanguenat and D. Seebach, *Stereoselective Chain Elongation at C–3 of Cysteine through 2,3–Dihydrothiazoles, Without Racemization. Preparation of 2–Amino–5–hydroxy–3–mercapto alkanoic Acid Derivatives*. 1991, J. Chem. Soc. Perkin Trans. 1, 2291–8.
G. Pattenden, S. Thom, and M. Jones, *Enantioselective Synthesis of 2–Alkyl Substituted Cysteines.* 1993, Tetrahedron, 49, 2131.
D. Bredt and S. Snyder, *Isolation of nitric oxide synthetase, a calmodulin–requiring enzyme.* 1990 Proc. Natl. Acad. Sci. U.S.A., 87, 682–685.
Moore et al, *2–Iminopiperidine and Other 2–Iminoazaheterocycles as Potent Inhibitors of Human Nitric Oxide Synthase Isoforms* 1996 J. Med. Chem., 39, 669–672.
T. Misko et al, *A Fluorometric Assay for the Measurement of Nitrite in Biological Samples* 1993, Analytical Biochemistry, 214, 11–16.
Y. Lee et al., *Conformationally–restricted Arginine Analogues as Alternative Substrates and Inhibitors of Nitric Oxide Synthases* 1999 Bioorg. Med. Chem. 7 1097–1104.
R. Young et al., *Inhibition of Inducible Nitric Oxide Synthase by Acetamidine Derivatives of Hetero–Substituted Lysine and Homolysine* 2000 Bioorg. Med. Chem. Lett. 10 597–600.

Primary Examiner—Joseph K. McKane
Assistant Examiner—Andrea D. Small
(74) Attorney, Agent, or Firm—Philip B. Polster, II

(57) ABSTRACT

The present invention contains halogenated 2-amino-3,4 heptenoic acid derivatives useful as nitric oxide synthase inhibitors.

77 Claims, No Drawings

US 6,586,471 B1

HALOGENATED 2-AMINO-3, 4 HEPTENOIC ACID DERIVATIVES USEFUL AS NITRIC OXIDE SYNTHASE INHIBITORS

This application claims the benefit of U.S. Provisional Application No. 60/197,027, filed Apr. 13, 2000.

FIELD OF THE INVENTION

The present invention relates to halogenated amidino compounds and their use in therapy, in particular their use as nitric oxide synthase inhibitors.

RELATED ART

It has been known since the early 1980's that the vascular relaxation caused by acetylcholine is dependent on the vascular endothelium. The endothelium-derived relaxing factor (EDRF), now known to be nitric oxide (NO) is generated in the vascular endothelium by nitric oxide synthase (NOS). The activity of NO as a vasodilator has been known for well over 100 years. In addition, NO is the active species deriving from amylnitrite, glyceryltrinitrate and other nitrovasodilators. The identification of EDRF as NO has coincided with the discovery of a biochemical pathway by which NO is synthesized from the amino acid L-arginine by the enzyme NO synthase.

Nitric oxide is an endogenous stimulator of the soluble guanylate cyclase. In addition to endothelium-dependent relaxation, NO is involved in a number of biological actions including cytotoxicity of phagocytic cells and cell-to-cell communication in the central nervous system.

There are at least three types of NO synthase as follows:

(i) a constitutive, $Ca^{++}$/calmodulin dependent enzyme, located in the endothelium, that releases NO in response to receptor or physical stimulation.

(ii) a constitutive, $Ca^{++}$/calmodulin dependent enzyme, located in the brain, that releases NO in response to receptor or physical stimulation.

(iii) a $Ca^{++}$ independent enzyme which is induced after activation of vascular smooth muscle, macrophages, endothelial cells, and a number of other cells by endotoxin and cytokines. Once expressed, this inducible nitric oxide synthase (hereinafter "iNOS") generates NO continuously for long periods.

The NO released by each of the two constitutive enzymes acts as a transduction mechanism underlying several physiological responses. The NO produced by the inducible enzyme is a cytotoxic molecule for tumor cells and invading microorganisms. It also appears that adverse effects of excess NO production, in particular pathological vasodilation and tissue damage, may result largely from the NO synthesized by iNOS.

There is a growing body of evidence that NO may be involved in the degeneration of cartilage which takes place as a result of certain conditions such as arthritis and it is also known that NO synthesis is increased in rheumatoid arthritis and in osteoarthritis.

Some of the NO synthase inhibitors proposed for therapeutic use are non-selective; they inhibit both the constitutive and the inducible NO synthases. Use of such a non-selective NO synthase inhibitor requires that great care be taken in order to avoid the potentially serious consequences of over-inhibition of the constitutive NO-synthase, such consequences including hypertension and possible thrombosis and tissue damage. In particular, in the case of the therapeutic use of L-NMMA (a non-selective NO synthase inhibitor) for the treatment of toxic shock it has been recommended that the patient must be subject to continuous blood pressure monitoring throughout the treatment. Thus, while non-selective NO synthase inhibitors have therapeutic utility provided that appropriate precautions are taken, NO synthase inhibitors which are selective in the sense that they inhibit the inducible NO synthase to a considerably greater extent than the constitutive isoforms of NO synthase would be of even greater therapeutic benefit and easier to use (S. Moncada and E. Higgs, FASEB J., 9, 1319–1330, 1995).

The following individual publications disclose compounds that inhibit-nitric oxide synthesis and preferentially inhibit the inducible isoform of nitric oxide synthase:

International Publication No. WO 96/35677
International Publication No. WO 96/33175
International Publication No. WO 96/151201
International Publication No. WO 95/11014
International Publication No. WO 95/11231
International Publication No. WO 95/25717
International Publication No. WO 95/24382
International Publication No. WO94/12165
International Publication No. WO94/14780
International Publication No. WO93/13055
European Patent Application No. EP0446699A1
U.S. Pat. No. 5,132,453
U.S. Pat. No 5,684,008
U.S. Pat. No. 5,830,917
U.S. Pat. No. 5,854,251
U.S. Pat. No. 5,863,931
U.S. Pat. No. 5,919,787
U.S. Pat. No. 5,945,408
U.S. Pat. No. 5,981,511

International Publication No. WO 95/25717 discloses certain amidino derivatives as being useful in inhibiting inducible nitric oxide synthase.

Various attempts have been made to improve the potency and selectivity of NOS inhibitors by adding one or more rigidifying elements to the inhibitor's structure. Publications by Y. Lee et al (*Bioorg. Med. Chem.* 7, 1097 (1999)) and R. J. Young et al (*Bioorg. Med. Chem. Lett.* 10, 597 (2000)) teach that imposing conformational rigidity with one or more carbon-carbon double bonds is not a favorable approach to impart selectivity for NOS inhibitors.

SUMMARY OF THE INVENTION

Compounds have now been found which have the advantage of being very efficacious as iNOS inhibitors in the human cartilage explant assay, a model for osteoarthritis.

The present invention demonstrates that a halogenated carbon-carbon double bond can be used as a rigidifying element, and the resulting compounds have unexpected potency and selectivity for inhibition of inducible NOS.

Compounds of the present invention are unexpectedly potent and highly selective inhibitors of inducible nitric oxide synthase, and exhibit a relatively long half life in vivo. The compounds of the present invention may therefore optionally be administered efficaciously in divided doses, such as, for example, every other day or twice per week.

In a broad aspect, the present invention is directed to novel compounds, pharmaceutical compositions and methods of using said compounds and compositions for inhibiting or modulating nitric oxide synthesis in a subject in need of such inhibition or modulation by administering a compound which preferentially inhibits or modulates the inducible isoform of nitric oxide synthase over the constitutive isoforms of nitric oxide synthase. It is also another object of the present invention to lower nitric oxide levels in a subject in need of such lowering. The present compounds possess useful nitric oxide synthase inhibiting activity, and are expected to be useful in the treatment or prophylaxis of a disease or condition in which the synthesis or over-synthesis of nitric oxide forms a contributory part.

In one embodiment of the present invention, the compounds are represented by Formulas I, II and III:

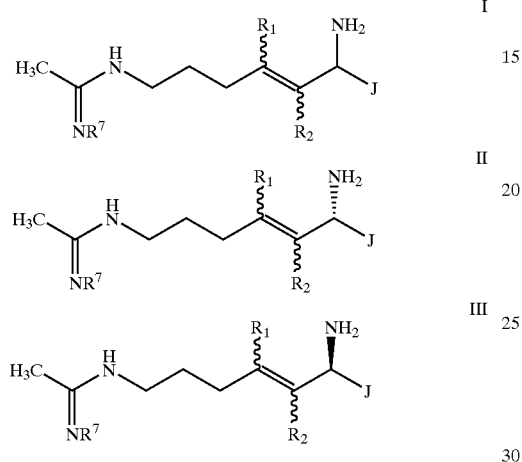

or a pharmaceutically acceptable salt thereof, wherein:
$R_1$ and $R_2$ are selected from the group consisting of H, alkyl, alkenyl, alkynyl, and halo wherein all but hydrogen and halo may be substituted by one or more hydroxy, alkyl, alkenyl, alkynyl, alkoxy, and halo;
$R^7$ is selected from the group consisting of H hydroxy, and alkoxy; and
J is selected from the group consisting of H, carboxyl, carboalkoxy, and $C(O)NR^3R^4$ wherein;
$R^3$ is selected from the group consisting of H, lower alkyl, lower alkylenyl and lower alkynyl; and
$R^4$ is selected from the group consisting of H, and a heterocyclic ring in which at least one member of the ring is carbon and in which 1 to about 4 heteroatoms are independently selected from oxygen, nitrogen and sulfur and said heterocyclic ring may be optionally substituted with heteroarylamino, N-aryl-N-alkylamino, N-heteroarylamino-N-alkylamino, haloalkylthio, alkanoyloxy, alkoxy, heteroaralkoxy, cycloalkoxy, cycloalkenyloxy, hydroxy, amino, thio, nitro, lower alkylamino, alkylthio, alkylthioalkyl, arylamino, aralkylamino, arylthio, alkylsulfinyl, alkylsulfonyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkylenedioxy, haloalkylenedioxy, cycloalkyl, cycloalkenyl, lower cycloalkylalkyl, lower cycloalkenylalkyl, halo, haloalkyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, cyanoalkyl, dicyanoalkyl, carboxamidoalkyl, dicarboxamidoalkyl, cyanocarboalkoxyalkyl, carboalkoxyalkyl, dicarboalkoxyalkyl, cyanocycloalkyl, dicyanocycloalkyl, carboxamidocycloalkyl, dicarboxamidocycloalkyl, carboalkoxycyanocycloalkyl, carboalkoxycycloalkyl, dicarboalkoxycycloalkyl, formylalkyl, acylalkyl, dialkoxyphosphonoalkyl, diaralkoxyphosphonoalkyl, phosphonoalkyl, dialkoxyphosphonoalkoxy, diaralkoxyphosphonoalkoxy, phosphonoalkoxy, dialkoxyphosphonoalkylamino, diaralkoxyphosphonoalkylamino, phosphonoalkylamino, dialkoxyphosphonoalkyl, diaralkoxyphosphonoalkyl, guanidino, amidino, and acylamino.; with the proviso that at least one of $R_1$ or $R_2$ must contain a halogen.

In another embodiment of the present invention, a novel intermediate compound is represented by Formula IV:

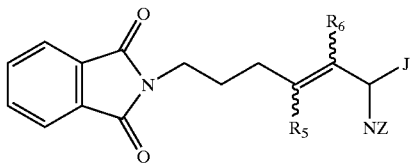

wherein
$R^5$ is selected from the group consisting of H, F, and methyl;
$R^6$ is selected from the group consisting of H, F, and methyl;
with the proviso that either $R^5$ or $R^6$ must be F.
J is selected from the group consisting of H, carboxyl, carboalkoxy, and $C(O)NR^3R^4$ wherein;
$R^3$ is selected from the group consisting of H, lower alkyl, lower alkylenyl and lower alkynyl; and $R^4$ is selected from the group consisting of H, and a heterocyclic ring in which at least one member of the ring is carbon and in which 1 to about 4 heteroatoms are independently selected from oxygen, nitrogen and sulfur and said heterocyclic ring may be optionally substituted with heteroarylamino, N-aryl-N-alkylamino, N-heteroarylamino-N-alkylamino, haloalkylthio, alkanoyloxy, alkoxy, heteroaralkoxy, cycloalkoxy, cycloalkenyloxy, hydroxy, amino, thio, nitro, lower alkylamino, alkylthio, alkylthioalkyl, arylamino, aralkylamino, arylthio, alkylsulfinyl, alkylsulfonyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkylenedioxy, haloalkylenedioxy, cycloalkyl, cycloalkenyl, lower cycloalkylalkyl, lower cycloalkenylalkyl, halo, haloalkyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, cyanoalkyl, dicyanoalkyl, carboxamidoalkyl, dicarboxamidoalkyl, cyanocarboalkoxyalkyl, carboalkoxyalkyl, dicarboalkoxyalkyl, cyanocycloalkyl, dicyanocycloalkyl, carboxamidocycloalkyl, dicarboxamidocycloalkyl, carboalkoxycyanocycloalkyl, carboalkoxycycloalkyl, dicarboalkoxycycloalkyl, formylalkyl, acylalkyl, dialkoxyphosphonoalkyl, diaralkoxyphosphonoalkyl, phosphonoalkyl, dialkoxyphosphonoalkoxy, diaralkoxyphosphonoalkoxy, phosphonoalkoxy, dialkoxyphosphonoalkylamino, diaralkoxyphosphonoalkylamino, phosphonoalkylamino, dialkoxyphosphonoalkyl, diaralkoxyphosphonoalkyl, guanidino, amidino, and acylamino.

Q is H, or an appropriate nitrogen protecting moiety such as, for example, t-butoxycarbonyl, 2-(4-biphenylyl) propyl(2)oxycarbonyl (Bpoc), 2-nitro-phenylsulfenyl (Nps) or dithia-succionyl.

DETAILED DESCRIPTION OF THE INVENTION

The present invention provides compounds having a halogenated carbon-carbon double bond, and these compounds have unexpected greater potency and selectivity for inhibition of inducible NOS.

Compounds of the present invention are unexpectedly potent and highly selective inhibitors of inducible nitric oxide synthase, and exhibit a relatively long half life in vivo as compared with known nitric oxide synthase inhibitors.

Compounds of Formulas I, II, III, IV, V and VI will be useful for treating, among other things, inflammation in a subject, or for treating other nitric oxide synthase-mediated disorders, such as, as an analgesic in the treatment of pain and headaches. The compounds of the present invention will be useful in the treatment of pain including somatogenic (either nociceptive or neuropathic), both acute and chronic, and could be used in a situation including neuropathic pain for which a common NSAID or opioid analgesic would traditionally be administered.

Conditions in which the compounds of the present invention will provide an advantage in inhibiting NO production from L-arginine include arthritic conditions. For example, compounds of the present invention will be useful to treat arthritis, including but not limited to rheumatoid arthritis, spondyloarthropathies, gouty arthritis, osteoarthritis, systemic lupus erythematosus, juvenile arthritis, acute rheumatic arthritis, enteropathic arthritis, neuropathic arthritis, psoriatic arthritis, and pyogenic arthritis.

Compounds of the invention will be further useful in the treatment of asthma, bronchitis, menstrual cramps (e.g., dysmenorrhea), premature labor, tendinitis, bursitis, skin-related conditions such as psoriasis, eczema, burns, sunburn, dermatitis, pancreatitis, hepatitis, and post-operative inflammation including inflammation from ophthalmic surgery such as cataract surgery and refractive surgery. Compounds of the invention also would be useful to treat gastrointestinal conditions such as inflammatory bowel disease, Crohn's disease, gastritis, irritable bowel syndrome and ulcerative colitis.

Compounds of the invention would be useful in treating inflammation and tissue damage in such diseases as vascular diseases, migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury, myocardial ischemia, and the like. The compounds would also be useful in the treatment of ophthalmic diseases, such as glaucoma, retinitis, retinopathies, uveitis, ocular photophobia, and of inflammation and pain associated. with acute injury to the eye tissue. Of particular interest among the uses of the present inventive compounds is the treatment of glaucoma, especially where symptoms of glaucoma are caused by the production of nitric oxide, such as in nitric oxide-mediated nerve damage. The compounds would also be useful in the treatment of pulmonary inflammation, such as that associated with viral infections and cystic fibrosis. The compounds would also be useful for the treatment of certain central nervous system disorders, such as cortical dementias including Alzheimer's disease, and central nervous system damage resulting from stroke, ischemia and trauma. These compounds would also be useful in the treatment of allergic rhinitis, respiratory distress syndrome, endotoxin shock syndrome, and atherosclerosis. The compounds would also be useful in the treatment of pain, including but not limited to postoperative pain, dental pain, muscular pain, pain caused by temporalmandibular joint syndrome, and pain resulting from cancer. The compounds would be useful for the prevention of dementias, such as Alzheimer's disease.

Besides being useful for human treatment, these compounds are also useful for veterinary treatment of companion animals, exotic animals and farm animals, including mammals and other vertebrates. More preferred animals include horses, dogs, and cats.

The present compounds may also be used in co-therapies, partially or completely, in place of other conventional anti-inflammatory therapies, such as together with steroids, NSAIDs, COX-2 selective inhibitors, matrix metalloproteinase inhibitors, 5-lipoxygenase inhibitors, $LTB_4$ antagonists and $LTA_4$ hydrolase inhibitors.

Other conditions in which the compounds of the present invention will provide an advantage in inhibiting NO inhibition include cardiovascular ischemia, diabetes (type I or type II), congestive heart failure, myocarditis, atherosclerosis, migraine, glaucoma, aortic aneurysm, reflux esophagitis, diarrhea, irritable bowel syndrome, cystic fibrosis, emphysema, asthma, bronchiectasis, hyperalgesia (allodynia), cerebral ischemia (both focal ischemia, thrombotic stroke and global ischemia (for example, secondary to cardiac arrest), multiple sclerosis and other central nervous system disorders mediated by NO, for example Parkinson's disease. Further neurodegenerative disorders in which NO inhibition may be useful include nerve degeneration or nerve necrosis in disorders such as hypoxia, hypoglycemia, epilepsy, and in cases of central nervous system (CNS) trauma (such as spinal cord and head injury), hyperbaric oxygen convulsions and toxicity, dementia, such as, for example pre-senile dementia, and AIDS-related dementia, cachexia, Sydenham's chorea, Huntington's disease, Amyotrophic Lateral Sclerosis, Korsakoff's disease, imbecility relating to a cerebral vessel disorder, sleeping disorders, schizophrenia, depression, depression or other symptoms associated with Premenstrual Syndrome (PMS), anxiety and septic shock.

Still other disorders or conditions which will be advantageously treated by the compounds of the present invention include treatment of prevention of opiate tolerance in patients needing protracted opiate analgesics, and benzodiazepine tolerance in patients taking benzodiazepines, and other addictive behavior, for example, nicotine addiction, alcoholism, and eating disorders. The compounds and methods of the present invention will also be useful in the treatment or prevention of drug withdrawal symptoms, for example treatment or prevention of symptoms of withdrawal from opiate, alcohol, or tobacco addiction. The present inventive compounds may also be useful to prevent tissue damage when therapeutically combined with antibacterial or antiviral agents.

The compounds of the present invention will also be useful in inhibiting NO production from L-arginine including systemic hypotension associated with septic and/or toxic hemorrhagic shock induced by a wide variety. of agents; therapy with cytokines such as TNF, IL-1 and IL-2; and as an adjuvant to short term immunosuppression in transplant therapy.

Compounds of the invention are useful for the prevention or treatment of cancer, such as colorectal cancer, and cancer of the breast, lung, prostate, bladder, cervix and skin. The present invention is further directed to the use of the compounds of the present invention for the treatment and prevention of neoplasias. The neoplasias that will be treatable or preventable by the compounds and methods of the present invention include brain cancer, bone cancer, a leukemia, such as, for example chronic lymphocytic leukemia, a lymphoma, epithelial cell-derived neoplasia (epithelial carcinoma) such as basal cell carcinoma, adenocarcinoma, gastrointestinal cancer such as lip cancer, mouth cancer, esophogeal cancer, small bowel cancer and stomach cancer, colon cancer, liver cancer, bladder cancer, pancreas cancer, urogenital cancers, such as ovary cancer, cervical cancer, vulvar cancer, and lung cancer, breast cancer and skin cancer, such as squamous cell, melanoma, and basal cell cancers, prostate cancer, renal cell carcinoma, and other known cancers that effect epithelial cells throughout the body. Compounds of the present invention will be effective as well for treatment of mesenchymal derived neoplasias. Preferably, the neoplasia to be treated is selected from gastrointestinal cancer, liver cancer, bladder cancer, pancreas cancer, ovary cancer, prostate cancer, cervical cancer, vulvar cancer, lung cancer, breast cancer and skin cancer, such as squamous cell and basal cell cancers. The present compounds and methods can also be used to treat the fibrosis which occurs with radiation therapy. The present compounds. and methods can be used to treat subjects having adenomatous polyps, including those with familial adenomatous polyposis (FAP). Additionally, the present compounds and methods can be used to prevent polyps from forming in patients at risk of FAP.

Conjunctive treatment of a compound of the present invention with another antineoplastic agent will produce a synergistic effect or alternatively reduce the toxic side effects associated with chemotherapy by reducing the therapeutic dose of the side effect-causing agent needed for therapeutic efficacy or by directly reducing symptoms of toxic side effects caused by the side effect-causing agent. A compound of the present invention will further be useful as an adjunct to radiation therapy to reduce side effects or enhance efficacy. In the present invention, another agent which can be combined therapeutically with a compound of the present invention includes any therapeutic agent which is capable of inhibiting the enzyme cyclooxygenase-2 ("COX-2"). Preferably such COX-2 inhibiting agents inhibit COX-2 selectively relative to the enzyme cyclooxygenase-1 ("COX-1"). Such a COX-2 inhibitor is known as a "COX-2 selective inhibitor". More preferably, a compound of the present invention can be therapeutically combined with a COX-2 selective inhibitor wherein the COX-2 selective inhibitor selectively inhibits COX-2 at a ratio of at least 10:1 relative to inhibition of COX-1, more preferably at least 30:1, and still more preferably at least 50:1 in an in vitro test. COX-2 selective inhibitors useful in therapeutic combination with the compounds of the present invention include celecoxib, valdecoxib, deracoxib, etoricoxib, rofecoxib, ABT-963 (2-(3,4-difluorophenyl)-4-(3-hydroxy-3-methyl-1-butoxy)-5-[4-(methylsulfonyl)phenyl-3(2H)-pyridazinone; described in PCT Patent Application No. WO 00/24719), or meloxicam. A compound of the present invention can also be advantageously used in therapeutic combination with a prodrug of a COX-2 selective inhibitor, for example parecoxib.

Another chemotherapeutic agent which will be useful in combination with a compound of the present invention can be selected, for example, from the following non-comprehensive and non-limiting list:

Alpha-difluoromethylornithine (DFMO), 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, tyrosine protein kinase inhibitors, Taiho UFT, uricytin, Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP (Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine,-Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin, trimelamol, Taiho 4181 -A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-Alb, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 zorubicin, alpha-carotene, alpha-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristo-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemex CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 471 1, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, elliprabin, elliptinium acetate, Tsumura EPMTC, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623,. leukoregulin, lonidamine, Lundbeck LU-23-112, Lilly LY-186641, NCI (US) MAP, marycin, Merrel Dow MDL-27048, Medco MEDR-340, merbarone, merocyanine derivatives, methylanilinoacridine, Molecular Genetics MGI-136, minactivin, mitonafide, mitoquidone, mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, octreotide, Ono ONO-112, oquizanocine, Akzo Org-10172, pancratistatin, pazelliptine, Warner-Lambert PD-111707, Warner-Lambert PD-15934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides, Yamanouchi YM-534, uroguanylin, combretastatin, dolastatin, idarubicin, epirubicin, estramustine, cyclophosphamide, 9-amino-2-(S)-camptothecin, topotecan, irinotecan (Camptosar), exemestane, decapeptyl (tryptorelin), or an omega-3 fatty acid.

Examples of radioprotective agents which may be used in a combination therapy with the compounds of this invention include AD-5, adchnon, amifostine analogues, detox, dimesna, 1-102, MM-159, N-acylated-dehydroalanines, TGF-Genentech, tiprotimod, amifostine, WR-151327, FUT-187, ketoprofen transdermal, nabumetone, superoxide dismutase (Chiron) and superoxide dismutase Enzon.

The compounds of the present invention will also be useful in treatment or prevention of angiogenesis-related disorders or conditions, for example, tumor growth, metastasis, macular degeneration, and atherosclerosis.

In a further embodiment, the present invention also provides therapeutic combinations for the treatment or prevention of ophthalmic disorders or conditions such as glaucoma. For example the present inventive compounds advantageously will be used in therapeutic combination with a drug which reduces the intraocular pressure of patients afflicted with glaucoma. Such intraocular pressure-reducing drugs include without limitation; latanoprost, travoprost, bimatoprost, or unoprostol. The therapeutic combination of a compound of the present invention plus an intraocular pressure-reducing drug will be useful because each is believed to achieve its effects by affecting a different mechanism.

In another combination of the present invention, the present inventive compounds can be used in therapeutic combination with an antihyperlipidemic or cholesterol-lowering drug such as a benzothiepine or a benzothiazepine antihyperlipidemic drug. Examples of benzothiepine antihyperlipidemic drugs useful in the present inventive therapeutic combination can be found in U.S. Pat. No. 5,994,391, herein incorporated by reference. Some benzothiazepine antihyperlipidemic drugs are described in WO 93/16055. Alternatively, the antihyperlipidemic or cholesterol-lowering drug useful in combination with a compound of the present invention can be an HMG Co-A reductase inhibitor. Examples of HMG Co-A reductase inhibitors useful in the present therapeutic combination include, individually, benfluorex, fluvastatin, lovastatin, provastatin, simvastatin, atorvastatin, cerivastatin, bervastatin, ZD-9720 (described in PCT Patent Application No. WO 97/06802), ZD-4522 (CAS No. 147098-20-2 for the calcium salt; CAS No. 147098-18-8 for the sodium salt; described in European Patent No. EP 521471), BMS 180431 (CAS No. 129829-03-4), or NK-104 (CAS No. 141750-63-2). The therapeutic combination of a compound of the present invention plus an antihyperlipidemic or cholesterol-lowering drug will be useful, for example, in reducing the risk of formation of atherosclerotic lesions in blood vessels. For example, atherosclerotic lesions often initiate at inflamed sites in blood vessels. It is established that antihyperlipidemic or cholesterol-lowering drug reduce risk of formation of atherosclerotic lesions by lowering lipid levels in blood. Without limiting the invention to a single mechanism of action, it is believed that one way the compounds of the present combination will work in concert to provide improved control of atherosclerotic lesions by, for example, reducing inflammation of the blood vessels in concert with lowering blood lipid levels.

In another embodiment of the invention, the present compounds can be used in combination with other compounds or therapies for the treatment of central nervous conditions or disorders such as migraine. For example, the present compounds can be used in therapeutic combination with caffeine, a 5-HT-1B/1D agonist (for example, a triptan such as sumatriptan, naratriptan, zolmitriptan, rizatriptan, almotriptan, or frovatriptan), a dopamine D4 antagonist (e.g., sonepiprazole), aspirin, acetaminophen, ibuprofen, indomethacin, naproxen sodium, isometheptene, dichloralphenazone, butalbital, an ergot alkaloid (e.g., ergotamine, dihydroergotamine, bromocriptine, ergonovine, or methyl ergonovine), a tricyclic antidepressant (e.g., amitriptyline or nortriptyline), a serotonergic antagonist (e.g., methysergide or cyproheptadine), a beta-andrenergic antagonist (e.g., propranolol, timolol, atenolol, nadolol, or metprolol), or a monoamine oxidase inhbitor (e.g., phenelzine or isocarboxazid). A further embodiment provides a therapeutic combination of a compound of the present invention with an opioid compound. Opioid compounds useful in this combination include without limitation morphine, methadone, hydromorphone, oxymorphone, levorphanol, levallorphan, codeine, dihydrocodeine, dihydrohydroxycodeinone, pentazocine, hydrocodone, oxycodone, nalmefene, etorphine, levorphanol, fentanyl, sufentanil, DAMGO, butorphanol, buprenorphine, naloxone, naltrexone, CTOP, diprenorphine, beta-funaltrexamine, naloxonazine, nalorphine, pentazocine, nalbuphine, naloxone benzoylhydrazone, bremazocine, ethylketocyclazocine, U50,488, U69,593, spiradoline, norbinaltorphimine, naltrindole, DPDPE, [D-la$^2$, glu$^4$] deltorphin, DSLET, met-enkephalin, leu-enkaphalin, beta-endorphin, dynorphin A, dynorphin B, and alpha-neoendorphin. An advantage to the combination of the present invention with an opioid compound is that the present inventive compounds will allow a reduction in the dose of the opioid compound, thereby reducing the risk or severity of opioid side effects, such as opioid addiction.

The term "alkyl", alone or in combination, means an acyclic alkyl radical, linear or branched, preferably containing from I to about 10 carbon atoms, more preferably containing from 1 to about 6 carbon atoms, and still more preferably about 1 to 3 carbon atoms. "Alkyl" also encompasses cyclic alkyl radicals containing from 3 to about 7 carbon atoms, preferably from 3 to 5 carbon atoms. Said alkyl radicals can be optionally substituted with groups as defined below. Examples of such radicals include methyl, ethyl, chloroethyl, hydroxyethyl, n-propyl, isopropyl, n-butyl, cyanobutyl, isobutyl, sec-butyl, tert-butyl, pentyl, aminopentyl, iso-amyl, hexyl, octyl and the like.

The term "alkenyl" refers to an unsaturated, acyclic hydrocarbon radical, linear or branched, in so much as it contains at least one double bond. Such radicals containing from 2 to about 6 carbon atoms, preferably from 2 to about 4 carbon atoms, more preferably from 2 to about 3 carbon atoms. Said alkenyl radicals may be optionally substituted with groups as defined below. Examples of suitable alkenyl radicals include propenyl, 2-chloropropylenyl, buten-1-yl, isobutenyl, penten-1-yl, 2-methylbuten-1-yl, 3-methylbuten-1-yl, hexen-1-yl, 3-hydroxyhe n-1-yl, hepten-1-yl, and octen-1-yl, and the like.

The term "alkynyl" refers to an unsaturated, acyclic hydrocarbon radical, linear or branched, in so much as it contains one or more triple bonds, such radicals containing 2 to about 6 carbon atoms, preferably from 2 to about 4 carbon atoms, more preferably from 2 to about 3 carbon atoms. Said alkynyl radicals may be optionally substituted with groups as defined below. Examples of suitable alkynyl radicals include ethynyl, propynyl, hydroxypropynyl, butyn-1-yl, butyn-2-yl, pentyn-1-yl, pentyn-2-yl, 4-methoxypentyn-2-yl, 3-methylbutyn-1-yl, hexyn-1-yl, hexyn-2-yl, hexyn-3-yl, 3,3-dimethylbutyn-1-yl radicals and the like.

The term "alkoxy" embrace linear or branched oxy-containing radicals each having alkyl portions of 1 to about 6 carbon atoms, preferably 1 to about 3 carbon atoms, such as a methoxy radical. The term "alkoxyalkyl" also embraces alkyl radicals having one or more alkoxy radicals attached to the alkyl radical, that is, to form monoalkoxyalkyl and dialkoxyalkyl radicals. Examples of such radicals include methoxy, ethoxy, propoxy, butoxy and tert-butoxy alkyls. The "alkoxy" radicals may be further substituted with one or more halo atoms, such as fluoro, chloro or bromo, to provide "haloalkoxy" radicals. Examples of such radicals include fluoromethoxy, chloromethoxy, trifluoromethoxy, difluoromethoxy, trifluoroethoxy, fluoroethoxy, tetrafluoroethoxy, pentafluoroethoxy, and fluoropropoxy.

The term "alkylthio" embraces radicals containing a linear or branched alkyl radical, of 1 to about 6 carbon atoms, attached to a divalent sulfur atom. An example of "lower alkylthio" is methylthio ($CH_3$—S—).

The term "alkylthioalkyl" embraces alkylthio radicals, attached to an alkyl group. Examples of such radicals include methylthiomethyl.

The term "halo" means halogens such as fluorine, chlorine, bromine or iodine atoms.

The term "heterocyclyl" means a saturated or unsaturated mono- or multi-ring carbocycle wherein one or more carbon atoms is replaced by N, S, P, or O. This includes, for example, the following structures:

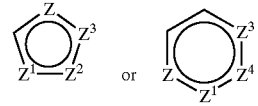

wherein Z, $Z^1$, $Z^2$ or $Z^3$ is C, S, P, O, or N, with the proviso that one of Z, $Z^1$, $Z^2$ or $Z^3$ is other than carbon, but is not O or S when attached to another Z atom by a double bond or when attached to another O or S atom. Furthermore, the optional substituents are understood to be attached to Z, $Z^1$, $Z^2$ or $Z^3$ only when each is C. The term "heterocyclyl" also includes fully. saturated ring structures such as piperazinyl, dioxanyl, tetrahydrofuranyl, oxiranyl, aziridinyl, morpholinyl, pyrrolidinyl, piperidinyl, thiazolidinyl, and others. The term "heterocyclyl" also includes partially unsaturated ring structures such as dihydrofuranyl, pyrazolinyl, imidazolinyl, pyrrolinyl, chromanyl, dihydrothiophenyl, and others.

The term "heteroaryl" means a fully unsaturated heterocycle.

In either "heterocycle" or "heteroaryl," the point of attachment to the molecule of interest can be at the heteroatom or elsewhere within the ring.

The term "cycloalkyl" means a mono- or multi-ringed carbocycle wherein each ring contains three to about seven carbon atoms, preferably three to about five carbon atoms. Examples include radicals such as cyclopropyl, cyclobutyl, cyclopentyl, cyclohexyl, cycloalkenyl, and cycloheptyl. The term "cycloalkyl" additionally encompasses spiro systems.

The term "oxo" means a doubly bonded oxygen.

The term "alkoxy" means a radical comprising an alkyl radical that is bonded to an oxygen atom, such as a methoxy radical. More preferred alkoxy radicals are "lower alkoxy" radicals having one to about ten carbon atoms. Still more preferred alkoxy radicals have one to about six carbon atoms. Examples of such radicals include methoxy, ethoxy, propoxy, isopropoxy, butoxy and tert-butoxy.

The term "aryl" means a fully unsaturated mono- or multi-ring carbocycle, including, but not limited to, substituted or unsubstituted phenyl, naphthyl, or anthracenyl.

The term "combination therapy" means the administration of two or more therapeutic agents to treat a therapeutic condition or disorder described in the present disclosure, for example atherosclerosis, pain, inflammation, migraine, neoplasia, angiogenisis-related condition or disorder, or other. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The phrase "therapeutically effective" is intended to include and qualify a combined amount of active ingredients in a combination therapy. This combined amount will achieve the goal of ameliorating the symptoms of, reducing or eliminating the targeted condition.

In its broadest embodiment, compounds of the present invention are represented by Formulas I, II and III

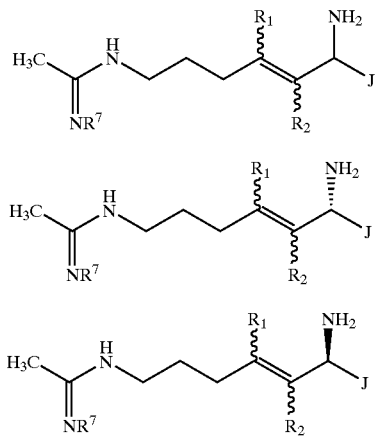

or pharmaceutically acceptable salts thereof, wherein:
$R_1$ is selected from the group consisting of hydrogen, alkyl, alkenyl, alkynyl, and halo wherein all but hydrogen and halo may be substituted by one or more hydroxy alkyl, alkenyl, alkynyl, alkoxy, and halo;
$R_2$ is selected from the group consisting of H, alkyl, alkenyl, alkynyl, and halo wherein all but hydrogen and halo may be substituted by one or more hydroxy, alkyl, alkenyl, alkynyl, alkoxy, and halo;
$R^7$ is selected from the group consisting of H and hydroxy; and
J is selected from the group consisting of hydroxy, carboxyl, carboalkoxy, and $C(O)NR^3R^4$ wherein;
$R^3$ is selected from the group consisting of H, lower alkyl, lower alkylenyl and lower alkynyl; and
$R^4$ is selected from the group consisting of H, and a heterocyclic ring in which at least one member of the ring is carbon and in which 1 to about 4 heteroatoms are independently selected from oxygen, nitrogen and sulfur and said heterocyclic ring may be optionally substituted with heteroarylamino, N-aryl-N-alkylamino, N-heteroarylamino-N-alkylamino, haloalkylthio, alkanoyloxy, alkoxy, heteroaralkoxy, cycloalkoxy; cycloalkenyloxy, hydroxy, amino, thio, nitro, lower alkylamino, alkylthio, alkylthioalkyl, arylamino, aralkylamino, arylthio, alkylsulfinyl, alkylsulfonyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkylenedioxy, haloalkylenedioxy, cycloalkyl, cycloalkenyl, lower cycloalkylalkyl, lower cycloalkenylalkyl, halo, haloalkyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, cyanoalkyl, dicyanoalkyl, carboxamidoalkyl, dicarboxamidoalkyl, cyanocarboalkoxyalkyl, carboalkoxyalkyl, dicarboalkoxyalkyl, cyanocycloalkyl, dicyanocycloalkyl, carboxamidocycloalkyl, dicarboxamidocycloalkyl, carboalkoxycyanocycloalkyl, carboalkoxycycloalkyl, dicarboalkoxycycloalkyl, formylalkyl, acylalkyl, dialkoxyphosphonoalkyl, diaralkoxyphosphonoalkyl, phosphonoalkyl, dialkoxyphosphonoalkoxy, diaralkoxyphosphonoalkoxy, phosphonoalkoxy, dialkoxyphosphonoalkylamino, diaralkoxyphosphonoalkylamino, phosphonoalkylamino, dialkoxyphosphonoalkyl, diaralkoxyphosphonoalkyl, guanidino, amidino, and acylamino; with the proviso that at least one of $R_1$ or $R_2$ must contain a halogen.

In another embodiment, compounds of the present invention are of Formula I, II or III wherein:
$R_1$ is halo; and
$R_2$ is selected from the group consisting of H, alkyl, alkenyl, alkynyl, and halo wherein all but hydrogen and halo may be substituted by one or more hydroxy, alkyl, alkenyl, alkynyl, alkoxy, and halo.

Another embodiment of the invention includes compounds of the present invention of Formula I, II or III wherein:
$R_1$ is selected from the group consisting of H, alkyl, alkenyl, alkynyl, and halo wherein all but hydrogen and halo may be substituted by one or more hydroxy, alkyl, alkenyl, alkynyl, alkoxy, and halo; and $R_2$ is halo.

In an additional embodiment, the invention includes compounds of the present invention of Formula I, II or III wherein:

$R_1$ is selected from the group consisting of halo or H;

$R_2$ is selected from the group consisting of halo or H;

with the proviso that at least one of $R_1$ or $R_2$ is halo.

In other embodiments, the invention includes compounds of the present invention of Formula I, II or III wherein:

$R_1$ is halo; and $R_2$ is selected from the group consisting of H, $C_1$–$C_3$ alkyl, and halo wherein all but hydrogen and halo may be substituted by one or more $C_1$–$C_3$ alkyl, $C_1$–$C_3$ alkoxy, and halo.

$R_1$ is selected from the group consisting of H, $C_1$–$C_3$ alkyl, and halo wherein all but H and halo may be substituted by one or more $C_1$–$C_3$ alkyl, $C_1$–$C_3$ alkoxy, and halo; and $R_2$ is halo.

$R_1$ is selected from the group consisting of halo or H; $R_2$ is selected from the group consisting of halo or H;

with the proviso that at least one of $R_1$ or $R_2$ is a halo.

$R_1$ is halo; and $R_2$ is halo.

$R_1$ is fluorine; and $R_2$ is fluorine.

Methods of using the compounds of Formula I, II or III include the use of inhibiting nitric oxide synthesis in a subject in need of such inhibition by administering a therapeutically effective amount of the present compound, selectively inhibiting nitric oxide synthesis produced by inducible nitric oxide synthase over nitric oxide produced by the constitutive forms of nitric oxide synthase in a subject in need of such inhibition by administering a therapeutically effective amount of a compound of Formula I, lowering nitric oxide levels in a subject in need of such by administering a therapeutically effective amount of a compound of Formula I, lowering nitric oxide levels in a subject in need of such by administering a therapeutically effective amount of a pharmaceutical composition comprising a compound of Formula I.

The term "pharmaceutically-acceptable salts" embraces salts commonly used to form alkali metal salts and to form addition salts of free acids or free bases. The nature of the salt is not critical, provided that it is pharmaceutically acceptable. Pharmaceutically acceptable salts are particularly useful as products of the methods of the present invention because of their greater aqueous solubility relative to a corresponding parent or neutral compound. Such salts must have a pharmaceutically acceptable anion or cation. Suitable pharmaceutically-acceptable acid addition salts of compounds of the present invention may be prepared from inorganic acid or from an organic acid. Examples of such inorganic acids are hydrochloric, hydrobromic, hydroiodic, nitric, carbonic, sulfuric and phosphoric acid. Appropriate organic acids include from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethylsulfonic, benzenesulfonic, sulfanilic, stearic, cyclohexylaminosulfonic, algenic, galacturonic acid. Suitable pharmaceutically-acceptable base addition salts of compounds of the present invention include metallic salts made from aluminum, calcium, lithium, magnesium, potassium, sodium and zinc or organic salts made from N,N'-dibenzylethylenediamine, choline, chloroprocaine, diethanol amine, ethylenediamine, meglumine (N-methylglucamine) and procain. Suitable pharmaceutically acceptable acid addition salts of the compounds of the present invention when possible include those derived from inorganic acids, such as hydrochloric, hydrobromic, boric, fluoroboric, phosphoric, metaphosphoric, nitric, carbonic (including carbonate and hydrogen carbonate anions), sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable pharmaceutically acceptable base salts include ammonium salts, alkali metal salts such as sodium and potassium salts, and alkaline earth salts such as magnesium and calcium salts. All of these salts may be prepared by conventional means from the corresponding conjugate base or conjugate acid of the compounds of the present invention by reacting, respectively, the appropriate acid or base with the conjugate base or conjugate acid of the compound. Another pharmaceutically acceptable salt is a resin-bound salt.

While it may be possible for the compounds of the present invention to be administered as the raw chemical, it is preferable to present them as a pharmaceutical composition. According to a further aspect, the present invention provides a pharmaceutical composition comprising a compound of the present invention or a pharmaceutically acceptable salt or solvate thereof, together with one or more pharmaceutically acceptable carriers thereof and optionally one or more other therapeutic ingredients. The carrier(s) must be acceptable in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a compound of The present invention or a pharmaceutically acceptable salt or solvate thereof with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example, saline, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

Preferred unit dosage formulations are those containing an effective dose, as hereinbelow recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavoring agents.

The compounds of the invention may be administered orally or via injection at a dose of from 0.001 to 200 mg/kg per day. The dose range for adult humans is generally from 0.005 mg to 10 g/day. Tablets or other forms of presentation provided in discrete units may conveniently contain an amount of compound of the invention which is effective at such dosage or as a multiple of the same, for instance, units containing 5 mg to 50 mg, usually around 1 mg to 20 mg.

The compounds of Formula I, II or III are preferably administered orally or by injection (intravenous or subcutaneous). The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity.

Compounds of the present invention can exist in tautomeric, geometric or stereoisomeric forms. The present invention contemplates all such compounds, including cis- and trans-geometric isomers and mixtures thereon, E- and Z-geometric isomers and mixtures thereof, R- and S-enantiomers, diastereomers, d-isomers, l-isomers, the racemic mixtures thereof and other mixtures thereof, as falling within the scope of the invention. Pharmaceutically acceptable salts of such tautomeric, geometric or stereoisomeric forms are also included within the invention.

The terms "cis" and "trans" denote a form of geometric isomerism in which two carbon atoms connected by a double bond will each have two highest ranking groups on the same side of the double bond ("cis" or "Z") or on opposite sides of the double bond ("trans" or "E"). Some of the compounds described contain alkenyl groups, and are meant to include both cis and trans or "E" and "Z" geometric forms.

Some of the compounds described contain one or more stereocenters and are meant to include R, S, and mixtures of R and S forms for each stereocenter present. Some of the compounds described contain one or more geometric isomers and are meant to include E, Z and mixtures of Z and E isomers.

The following general synthetic sequences are useful in making the present invention.

Scheme 1:

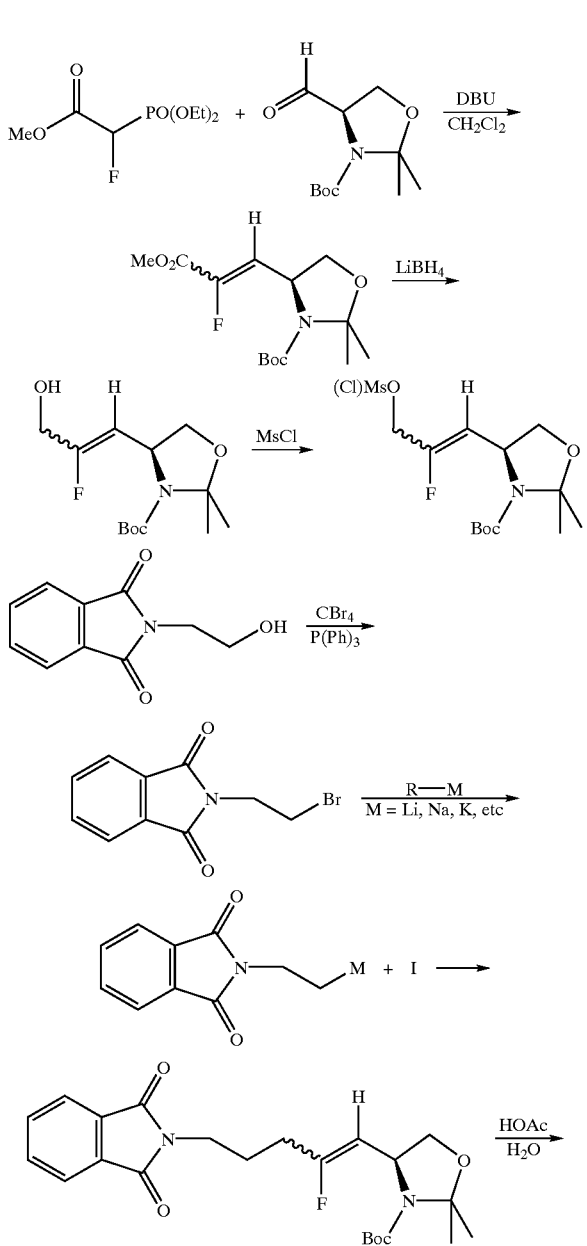

19
-continued
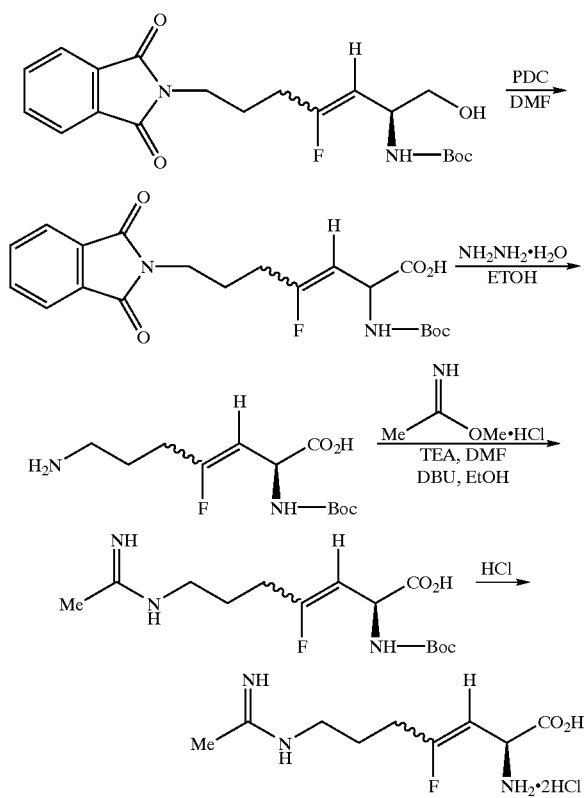
20
-continued
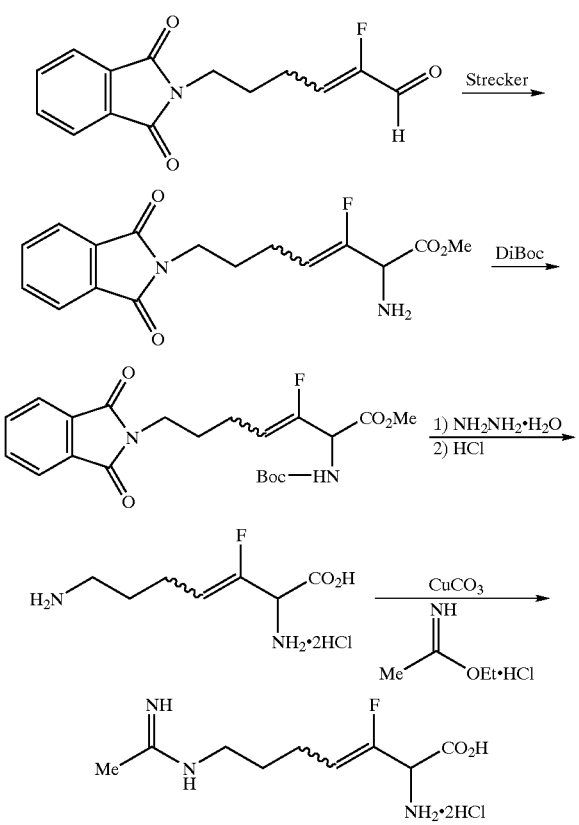
Scheme 2:
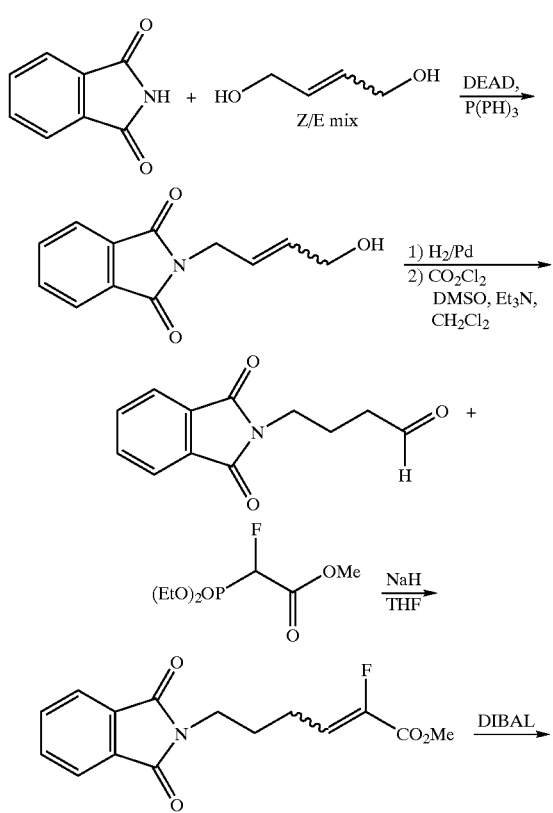
Scheme 3:
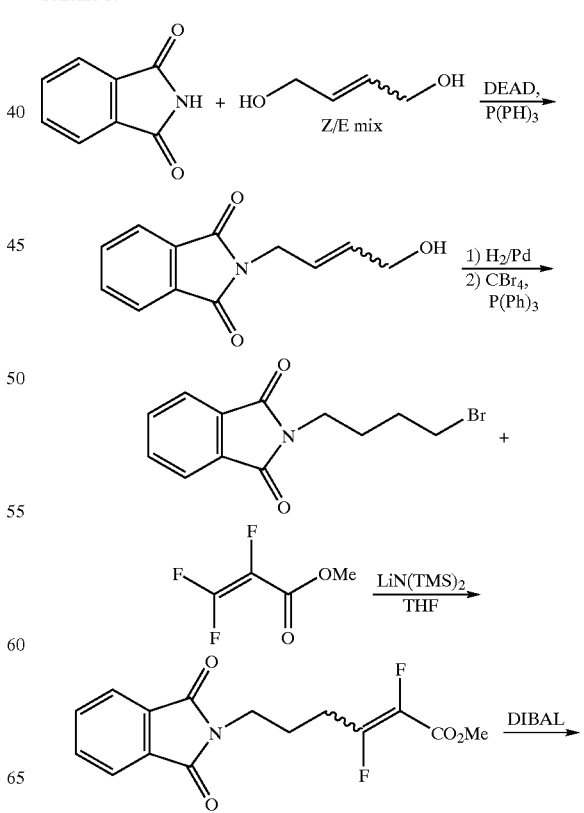

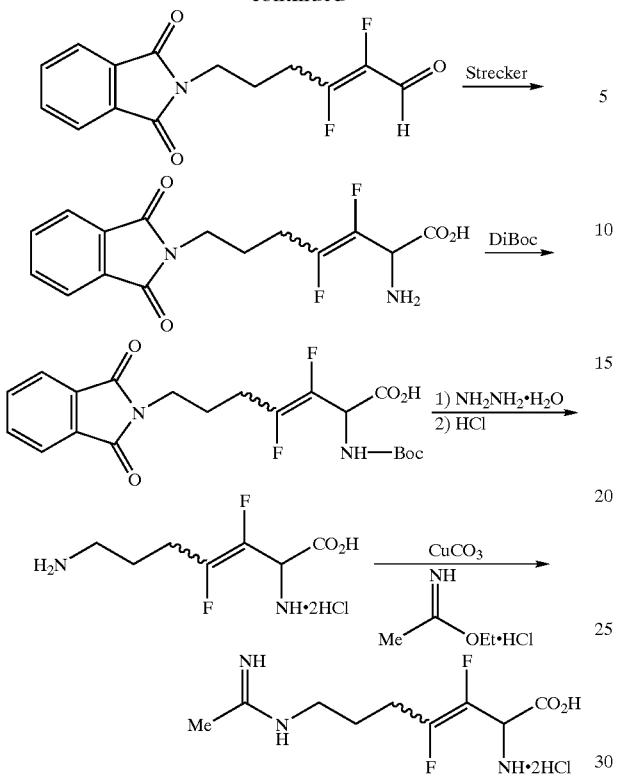

A novel intermediate compound of the present invention is represented by Formula IV:

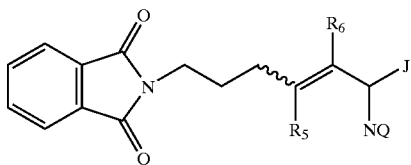

IV wherein
- $R^5$ is selected from the group consisting of H, F, and methyl;
- $R^6$ is selected from the group consisting of H, F, and methyl;
- with the proviso that either $R^5$ or $R^6$ must be F.
- J is selected from the group consisting of H, hydroxy, alkoxy, carboxy, carboalkoxy; and $NR^3R^4$ where $R^3$ is selected from the group consisting of H, lower alkyl, lower alkylenyl and lower alkynyl; and $R^4$ is selected from the group consisting of H, and a heterocyclic ring in which at least one member of the ring is carbon and in which 1 to about 4 heteroatoms are independently selected from oxygen, nitrogen and sulfur and said heterocyclic ring may be optionally substituted with heteroarylamino, N-aryl-N-alkylamino, N-heteroarylamino-N-alkylamino, haloalkylthio, alkanoyloxy, alkoxy, heteroaralkoxy, cycloalkoxy, cycloalkenyloxy, hydroxy, amino, thio, nitro, lower alkylamino, alkylthio, alkylthioalkyl, arylamino, aralkylamino, arylthio, alkylsulfinyl, alkylsulfonyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkylenedioxy, haloalkylenedioxy, cycloalkyl, cycloalkenyl, lower cycloalkylalkyl, lower cycloalkenylalkyl, halo, haloalkyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, cyanoalkyl, dicyanoalkyl, carboxamidoalkyl, dicarboxamidoalkyl, cyanocarboalkoxyalkyl, carboalkoxyalkyl, dicarboalkoxyalkyl, cyanocycloalkyl, dicyanocycloalkyl, carboxamidocycloalkyl, dicarboxamidocycloalkyl, carboalkoxycyanocycloalkyl, carboalkoxycycloalkyl, dicarboalkoxycycloalkyl, formylalkyl, acylalkyl, dialkoxyphosphonoalkyl, diaralkoxyphosphonoalkyl, phosphonoalkyl, dialkoxyphosphonoalkoxy, diaralkoxyphosphonoalkoxy, phosphonoalkoxy, dialkoxyphosphonoalkylamino, diaralkoxyphosphonoalkylamino, phosphonoalkylamino, dialkoxyphosphonoalkyl, diaralkoxyphosphonoalkyl, guanidino, amidino, and acylamino.

Q is H, or an appropriate nitrogen protecting moiety such as, for example, t-butoxycarbonyl, 2-(4-biphenylyl) propyl(2)oxycarbonyl (Bpoc), 2-nitro-phenylsulfenyl (Nps) or dithia-succionyl.

The following examples are provided to illustrate the present invention and are not intended to limit the scope thereof. Those skilled in the art will readily understand that known variations of the conditions and processes of the following preparative procedures can be used to prepare these compounds.

EXAMPLE 1

(2S,3Z)-2-amino-4-fluoro-7-[(1-iminoethyl)amino]-3-heptenoic acid, dihydrochloride

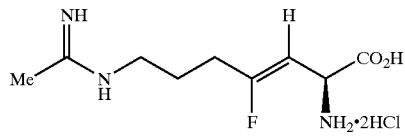

Example 1a

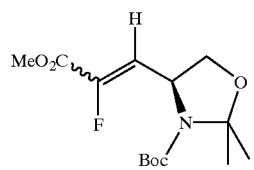

A $CH_2Cl_2$ solution of triethyl-2-fluoro-2-phosphono acetate is combined with a $CH_2Cl_2$ solution of DBU. To this stirred mixture is added drop-wise at room temperature a $CH_2Cl_2$ solution of Garner's aldehyde possessing the S stereochemistry illustrated. By alternatively employing Garner's aldehyde possessing R stereochemistry the R isomer of Example 1 is prepared following the procedures presented below. After stirring. this reaction at room temperature, all solvent is removed in vacuo, the residue is dissolved in EtOAc. This solution is then washed with KHSO₄ and brine before it is dried and stripped of all solvent under reduced pressure. The residue crude product is chromatographed to provide the illustrated fluoro acetate product as a mixture of E and Z isomers.

Example 1b

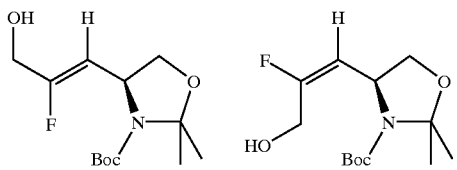

A THF solution of the product of Example 1a is cooled in an ice bath is reacted with LiBH₄ (2M solution in THF) and then allowed to warm to room temperature. After stirring at room temperature, the reaction is quenched with 10% KHSO₄ and then stripped of all solvent. The residue, dissolved in EtOAc, is washed with KHSO₄ and brine. After drying this solution it is stripped of all solvent under reduced pressure. The crude product residue mixture is chromatographed to yield the separated title Z and E isomeric fluoro alcohols pictured above.

Example 1c

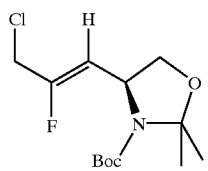

A solution of the Z isomer product of Example 1b in CH₂Cl₂ is cooled in an ice bath before being treated with an equivalent of triethylamine followed by an equivalent of methanesulfonyl chloride. The mixture is allowed to stir overnight before it is worked up to give the pictured allylic chloride product.

Example 1d

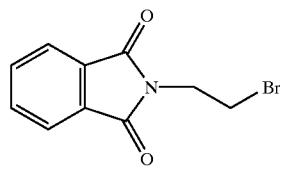

A solution of the phthalamidoethanol in CH₂Cl₂ is treated with carbon tetrabromide (CBr₄) and triphenylphosphine to yield the phthalamidoethyl bromide product illustrated.

Example 1e

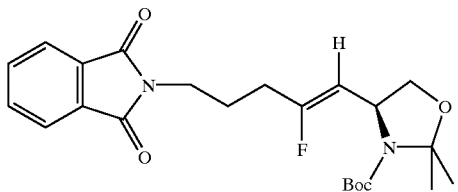

The product of Example 1d in THF at low temperature is treated with n-butyl lithium in THF. To this solution is added the product of Example 1c to afford the title phthalimido vinyl fluoride product after warming to room temperature and working up the reaction.

Example 1f

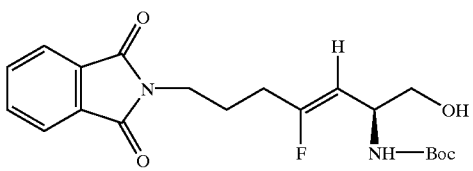

The product of Example 1e dissolved in aqueous acetic acid is stirred at room temperature to 45° C. until all starting material is hydrolyzed. All solvent is then removed in vacuo and the residue is chromatographed to produce the title alcohol.

Example 1g

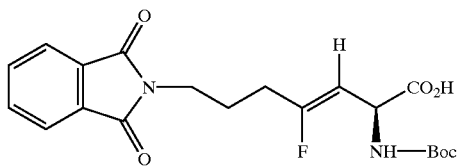

The product of Example 1f dissolved in DMF is treated with pyridinium dichromate (PDC) and this mixture is stirred at room temperature for 20 hrs. The reaction mixture is poured into water and this mixture is extracted with EtOAc. The organic wash is extracted with 5% KHCO₃ and this solution is acidified to pH 3 with 1N KHSO₄ before it is extracted with EtOAc. This solution is dried and stripped of all solvent under reduced pressure to yield the title product acid.

Example 1h

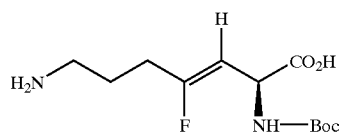

An EtOH solution of the product of Example 1g and hydrazine hydrate are refluxed overnight, cooled to room temperature, and stripped of all solvent under a stream of nitrogen. The residue is stirred with water that is acidified to pH 4 with glacial acetic acid. Removal of all solvent provides the title product.

Example 1i

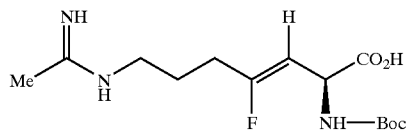

A solution of the product of Example 1h and triethyl amine in DMF is treated with methyl acetimidate hydrochloride. After stirring the solution for an hour, a second portion of imidate is added and this mix is stirred for an additional hour before another portion of imidate is added. This mixture is stirred for an additional 3 hr before it is worked up. The residue crude product mixture is chromatographed to yield the title Boc protected amino acid product.

Example 1

A solution of the product of Example 1i in HOAc is treated with 4N HCl in dioxane and allowed to stir at room temperature for an hour before all solvent is removed under a stream of nitrogen. The residue is lyophilized from water to generated the title compound.

Example 2

(2S,3E)-2-amino-4-fluoro-7-[(1-iminoethyl)amino]-3-heptenoic acid, dihydrochloride

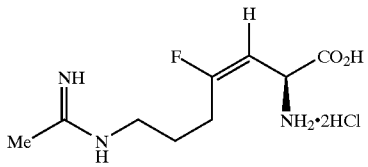

Example 2a

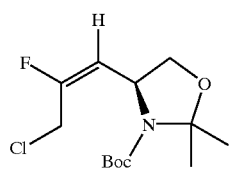

A solution of the E isomer product of Example 1b in $CH_2Cl_2$ is cooled in an ice bath before being treated with an equivalent of triethylamine followed by an equivalent of methanesulfonyl chloride. The mixture is allowed to stir overnight before it is worked up to give the pictured allylic chloride product.

Example 2b

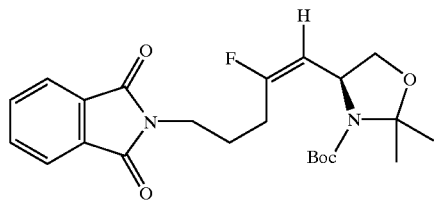

The product of Example 1d in THF at low temperature is treated with n-butyl lithium in THF. To this solution is added the product of Example 2a to afford the title product after warming to room temperature and working up the reaction.

Example 2c

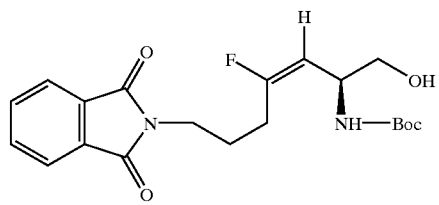

The product of Example 2b dissolved in aqueous acetic acid is stirred at room temperature to 45° C. until all starting material is hydrolyzed. All solvent is removed in vacuo and the residue is chromatographed to produce the title alcohol.

Example 2d

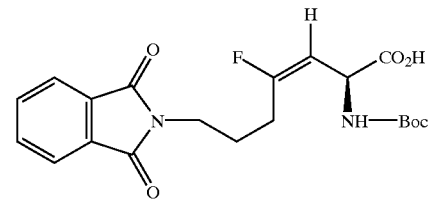

The product of Example 2c dissolved in DMF is treated with pyridinium dichromate (PDC) and this mixture is stirred at room temperature for 20 hrs. The reaction mixture is poured into water and this mixture is extracted with EtOAc. The organic wash is extracted with 5% $KHCO_3$ and this solution is acidified to pH 3 with 1N $KHSO_4$ before it is extracted with EtOAc. This solution is dried and stripped of all solvent under reduced pressure to yield the title product.

Example 2e

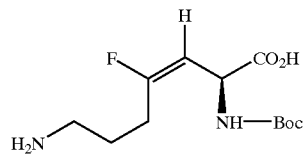

An EtOH solution of the product of Example 2d and hydrazine hydrate is refluxed overnight, cooled to room temperature, and stripped of all solvent under a stream of nitrogen. The residue is stirred with water that is acidified to pH 4 with glacial acetic acid. Removal of all solvent provides the title Boc protected amino acid product.

Example 2f

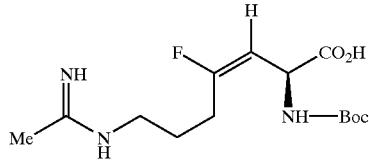

A solution of the product of Example 2e and triethyl amine in DMF is treated with methyl acetimidate hydrochloride. After stirring the solution for an hour, a second portion of imidate is added and this mix is stirred for an additional hour before another portion of imidate is added. This mixture is stirred for an additional 3 hr before it is worked up. The residue crude product mixture is chromatographed to yield the title Boc protected amino acid product.

Example 2

A solution of the product of Example 2f in HOAc is treated with 4N HCl in dioxane and allowed to stir at room temperature for an hour before all solvent is removed under a stream of nitrogen. The residue is lyophilized from water to generated the title compound.

Example 3

(3Z)-2-amino-3-fluoro-7-[(1-iminoethyl)amino]-3-heptenoic acid, dihydrochloride

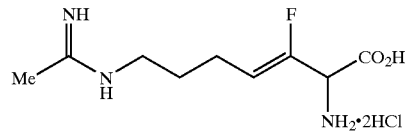

Example 3a

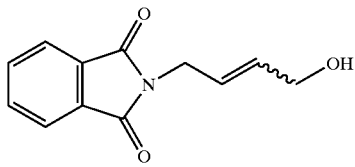

To a solution of phthalimide, 1,4 dihydroxy-2-butene and polymer-supported triphenylphosphine in THF is added dropwise dimethylazodicarboxylate. The reaction mixture is stirred at room temperature until analysis by thin layer chromatography shows that no starting material remains. The mixture is filtered through celite, and the filtrate is concentrated. The resulting residue is partitioned between CH$_2$Cl$_2$ and water. The organic layer is separated, washed with water and brine, dried over MgSO$_4$, filtered and concentrated. The crude material is purified by flash column chromatography on silica gel to give the desired alcohol as a Z/E mixture.

Example 3b

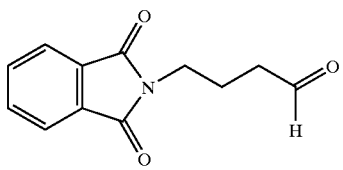

The product of Example 3a is hydrogenated over Pd/C. The heterogeneous reaction mixture is filtered and stripped of all solvent under reduced pressure to generate the saturated alcohol. This material without further purification and dissolved in CH$_2$Cl$_2$ is added to a cold mixture of oxalyl chloride and dimethyl sulfoxide. After stirring this mixture for 30 minutes triethyl amine is added. The reaction is stirred for an hour before it is diluted with water and the layers separated. The aqueous fraction is washed with hexane and the combined organic extracts are Washed with 5N HCl and saturated NaHCO$_3$, dried, and concentrated to produce the title aldehyde product illustrated above.

Example 3c

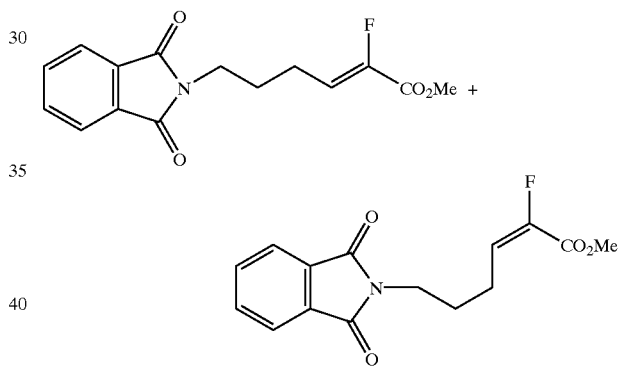

The product of Example 3b in a CH$_2$Cl$_2$ solution is reacted with triethyl-2-fluoro-2-phosphono acetate by the method of Example 1a to yield the Z and E mixture of fluoro acetates shown above. These products are separated by chromatography.

Example 3d

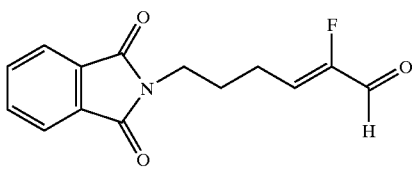

The Z isomer product of Example 3c in THF is reduced with diisobutyl aluminumhydride (DIBAL) to yield the illustrated aldehyde.

Example 3e

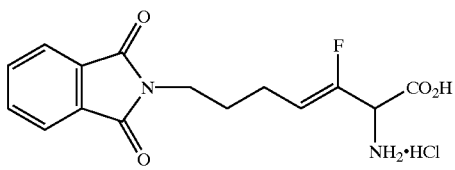

The aldehyde product of Example 3d is elaborated to the amino acid pictured above through a modification of the Strecker synthesis to yield either racemic or single isomer amino acid.

Example 3f

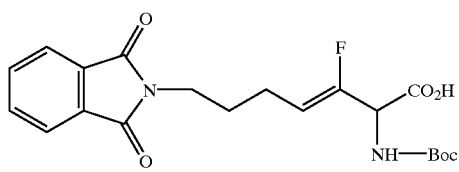

The amino acid product of Example 3e is converted to its Boc derivative illustrated above using di-t-butyl dicarbonate in the presence of base.

Example 3g

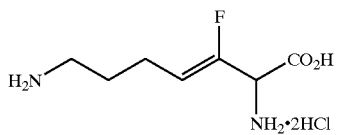

The Boc phthalimide product of Example 3f is reacted with hydrazine hydrate in ethanol to generate the free amine. This material is then treated with aqueous HCl to yield the title amino acid product shown.

Example 3

The amino acid product of Example 3g is then converted to the title product by the method of Example 1i.

Example 4

(3 E)-2-amino-3-fluoro-7-[(1-iminoethyl)amino]-3-heptenoic acid, dihydrochloride

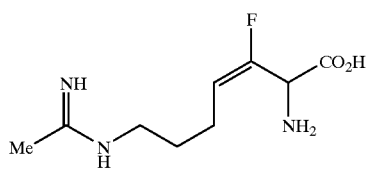

Example 4a

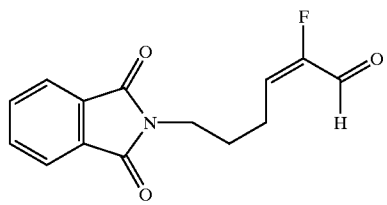

The E isomer product of Example 3c in THF is reduced with diisobutyl aluminumhydride (DIBAL) to produce the illustrated E configured aldehyde.

Example 4b

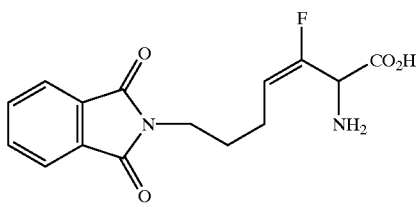

The aldehyde product of Example 4a is elaborated to the amino acid pictured above through a modification of the Strecker synthesis to yield either racemic or single isomer amino acid.

Example 4c

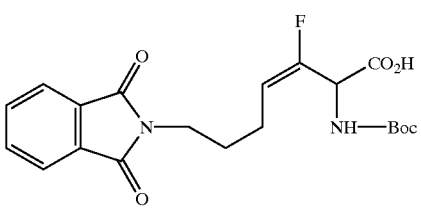

It The amino acid product of Example 4b is converted to its Boc derivative illustrated above using di-t-butyl dicarbonate in the presence of base.

Example 4d

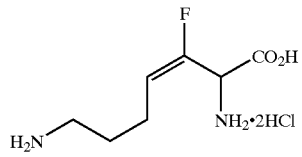

The Boc phthalimide product of Example 4c is treated with hydrazine hydrate in ethanol to generate the free amine. This material is then treated with aqueous HCl to yield the title amino acid dihydrochloride product shown.

Example 4

The amino acid product of Example 4d is then converted to the title product by the method of Example 1i.

Example 5

(3E)-2-amino-3,4-difluoro-7-[(1-iminoethyl)amino]-3-heptenoic acid, dihydrochloride

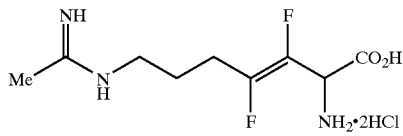

Example 5a

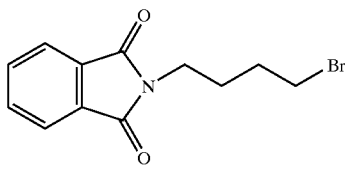

The product of Example 3a is hydrogenated over Pd/C. The heterogeneous reaction mixture is filtered and stripped of all solvent under reduced pressure to generate the saturated alcohol. This material without further purification is dissolved in $CH_2Cl_2$ and treated with triphenyl phosphine and carbon tetrabromide. This reaction is allowed to stir until the reaction is complete by TLC to produce the title bromide product illustrated above.

Example 5b

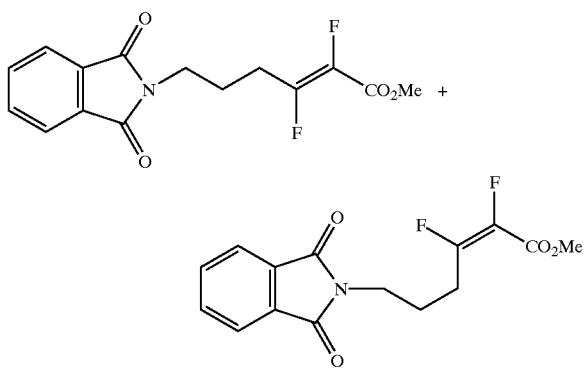

The product of Example 5a in THF and under an inert atmosphere is cooled before it is treated with sec-butyl lithium or lithium hexamethyldisylazide. To this solution is added methyl trifluoroacrylate. The reaction is allowed to warm to room temperature and the mixture of E and Z isomeric title products are separated by chromatography.

Example 5c

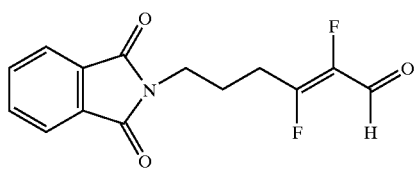

The E isomer product of Example 5b is reacted with DIBAL by the method of Example 3d to yield the pictured title aldehyde.

Example 5d (3E)-2-amino-3,4-difluoro-7-[(1-iminoethyl)amino]-3-heptenoic acid, dihydrochloride

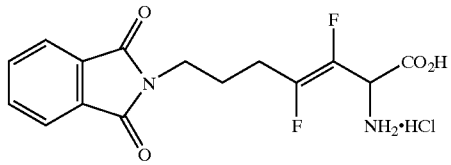

The product of Example 5c is converted to the title amino acid by the methods discussed and utilized in Example 3e.

Example 5e

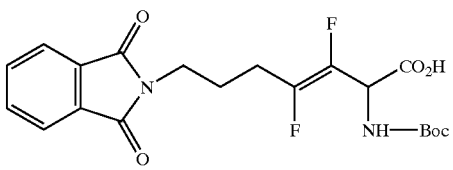

The product of Example 5d is converted to the Boc title material by the methods described in Example 3f.

Example 5f

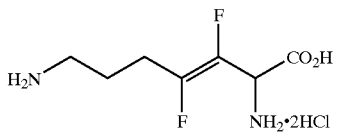

The title product of Example 5e is converted to the title material by the methods described in Example 3g.

Example 5

The amino acid product of Example 5f is then converted to the title product by the method of Example 1i.

Example 6

(3Z)-2-amino-3,4-difluoro-7-[(1-iminoethyl)amino]-3-heptenoic acid, dihydrochloride

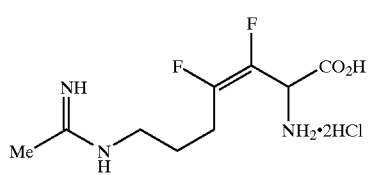

Example 6a

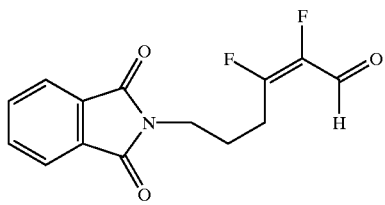

The Z isomer product of Example 5b is reacted with DIBAL by the method of Example 3d to yield the pictured title aldehyde.

Example 6b

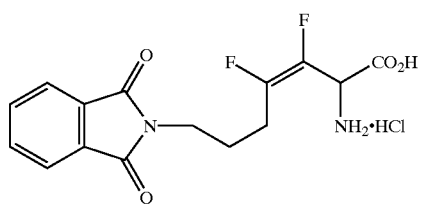

The product of Example 6a is converted to the title amino acid by the methods discussed and utilized in Example 3e.

Example 6c

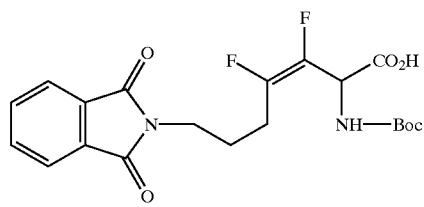

The product of Example 6b is converted to the Boc title material by the methods described in Example 3f.

Example 6d

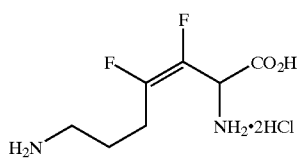

The title product of Example 6c is converted to the title material by the methods described in Example 3g.

Example 6

The amino acid product of Example 6d is then converted to the title product by the method of Example 1i.

A novel intermediate compound of the present invention is represented by formula IV:

IV wherein $R_5$ is selected from the group consisting of H, F, and methyl;

$R_6$ is selected from the group consisting of H, F, and methyl;

with the proviso that either $R_5$ or $R_6$ must be F.

J is selected from the group consisting of hydroxy, carboxyl; and $NR_3R_4$ where $R_3$ is selected from the group consisting of H, lower alkyl, lower alkylenyl and lower alkynyl; and $R_4$ is selected from the group consisting of H, and a heterocyclic ring in which at least one member of the ring is carbon and in which 1 to about 4 heteroatoms are independently selected from oxygen, nitrogen and sulfur and said heterocyclic ring may be optionally substituted with heteroarylamino, N-aryl-N-alkylamino, N-heteroarylamino-N-alkylamino, haloalkylthio, alkanoyloxy, alkoxy, heteroaralkoxy, cycloalkoxy, cycloalkenyloxy, hydroxy, amino, thio, nitro, lower alkylamino, alkylthio, alkylthioalkyl, arylamino, aralkylamino, arylthio, alkylsulfinyl, alkylsulfonyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkylenedioxy, haloalkylenedioxy, cycloalkyl, cycloalkenyl, lower cycloalkylalkyl, lower cycloalkenylalkyl, halo, haloalkyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, cyanoalkyl, dicyanoalkyl, carboxamidoalkyl, dicarboxamidoalkyl, cyanocarboalkoxyalkyl, carboalkoxyalkyl, dicarboalkoxyalkyl, cyanocycloalkyl, dicyanocycloalkyl, carboxamidocycloalkyl, dicarboxamidocycloalkyl, carboalkoxycyanocycloalkyl, carboalkoxycycloalkyl, dicarboalkoxycycloalkyl, formylalkyl, acylalkyl, dialkoxyphosphonoalkyl, diaralkoxyphosphonoalkyl, phosphonoalkyl, dialkoxyphosphonoalkoxy, diaralkoxyphosphonoalkoxy, phosphonoalkoxy, dialkoxyphosphonoalkylamino, diaralkoxyphosphonoalkylamino, phosphonoalkylamino, dialkoxyphosphonoalkyl, diaralkoxyphosphonoalkyl, guanidino, amidino, and acylamino, Z is an appropriate nitrogen protecting group such as, for example, t-butoxycarbonyl, 2-(4-biphenylyl)propyl(2) oxycarbonyl (Bpoc), 2-nitro-phenylsulfenyl (Nps) and dithia-succionyl. Numerous protected amino groups useful in the present invention for are described by Theodora W. Greene and Peter G. M. Wuts (*Protective Groups in Organic Synthesis,* 3rd ed., John Wiley & Sons, New York, 1999, pp. 494–653). For example NZ can be a 4-chlorobenzylimino group. In one embodiment of the present invention, the protected amino group is any such group resulting from the reaction of an aldehyde with the corresponding amino group to form a Schiff base. A large variety of deprotecting reagents can be advantageously used in the present invention to effect the conversion of the intermediate to the desired compound. Many such deprotecting reagents are described by Greene and Wuts, supra. For example, when the protected amino group is a 4-chlorobenzylimino group or a t-butoxycarbonylamino group, preferably the deprotecting reagent is an acid. Some useful acid deprotecting agents include, without limitation, hydrochloric acid, hydrobromic acid, sulfuric acid, trifluoroacetic acid, phosphoric acid, phosphorus acid, and acetic acid.

Biological Data

The activity of the above listed compounds can be determined in the following assays:

Citrulline Assay for Nitric Oxide Synthase

Nitric oxide synthase (NOS) activity is measured by monitoring the conversion of [$^3$H]-arginine to [$^3$H]-citrulline (Bredt and Snyder, *Proc. Natl. Acad. Sci. U.S.A.,* 87, 682–685, 1990 and Misko et al, *Eur. J. Pharm.,* 233, 119–125, 1993). Human inducible NOS (hiNOS), human endothelial constitutive NOS (hecNOS) and human neuronal constitutive NOS (hncNOS) are each cloned from RNA extracted from human tissue. The cDNA for human inducible NOS (hiNOS) is isolated from a lambda cDNA library made from RNA extracted from a colon sample from a patient with ulcerative colitis. The cDNA for human endothelial constitutive NOS (hecNOS) is isolated from a lambda cDNA library made from RNA extracted from human umbilical vein endothelial cells (HUVEC) and the cDNA for human neuronal constitutive NOS (hncNOS) is isolated from a lambda cDNA library made from RNA extracted from human cerebellum obtained from a cadaver. The recombinant enzymes are expressed in Sf9 insect cells using a baculovirus vector (Rodi et al, in *The Biology of Nitric Oxide Pt. 4: Enzymology, Biochemistry and Immunology:* Moncada, S., Feelisch, M., Busse, R., Higgs, E., Eds.; Portland Press Ltd.: London, 1995; pp 447–450). Enzyme activity is isolated from soluble cell extracts 25 and partially purified by DEAE-Sepharose chromatography. To measure NOS activity, 10 µL of enzyme is added to 40 µL of 50 mM Tris (pH 7.6) in the presence or absence of test compounds and the reaction initiated by the addition of 50 µL of a reaction mixture containing 50 mM Tris (pH 7.6), 2.0 mg/mL bovine serum albumin, 2.0 mM DTT, 4.0 mM CaCl$_2$, 20 µM FAD, 100 µM tetrahydrobiopterin, 0.4–2.0 mM NADPH and 60 µM L-arginine containing 0.9 µCi of L-[2,3-$^3$H]-arginine. The final concentration of L-arginine in the assay is 30 µM. For hecNOS or hncNOS, calmodulin is included at a final concentration of 40–100 nM. Following incubation at 37° C. for 15 minutes, the reaction is terminated by addition of 300 µL of cold stop buffer containing 10 mM EGTA, 100 mM HEPES, pH 5.5 and 1 mM citrulline. [3H]-Citrulline is separated by chromatography on Dowex 50W X-8 cation exchange resin and radioactivity determined with a liquid scintillation counter. Results are reported as the IC$_{50}$ values of compounds for hiNOS, hecNOS and hncNOS.

In Vivo Assay

Rats are treated with an intraperitoneal injection of 10–12.5 mg/kg of endotoxin (LPS) to induce systemic expression of inducible nitric oxide synthase, resulting in markedly elevated plasma nitrite/nitrate levels. Compounds are administered orally 1 hour prior to LPS administration and plasma nitrite/nitrate levels are determined 5 hours following LPS administration.

Raw Cell Nitrite Assay

RAW 264.7 cells can be plated to confluency on a 96-well tissue culture plate grown overnight (17 h) in the presence of LPS to induce NOS. A row of 3–6 wells can be left untreated and served as controls for subtraction of nonspecific background. The media can be removed from each well and the cells washed twice with Kreb-Ringers-Hepes (25 mM, pH 7.4) with 2 mg/ml glucose. The cells are then placed on ice and incubated with 50 mL of buffer containing L-arginine (30 mM) +/− inhibitors for 1 h. The assay can be initiated by warming the plate to 37° C. in a water bath for 1 h. Production of nitrite by intracellular iNOS will be linear with time. To terminate the cellular assay, the plate of cells can be placed on ice and the nitrite-containing buffer removed and analyzed for nitrite using a previously published fluorescent determination for nitrite. T. P. Misko et al, *Analytical Biochemistry,* 214, 11–16 (1993).

Human Cartilage Explant Assay

Bone pieces are rinsed twice with Dulbecco's Phosphate Buffered Saline (GibcoBRL) and once with Dulbecco's Modified Eagles Medium (GibcoBRL) and placed into a petri dish with phenol red free Minimum Essential Medium (MEM) (GibcoBRL). Cartilage was cut into small explants of approximately 25–45 mg in weight and one or two explants per well are placed into 48 well culture plates with 500 µL of culture media per well. The culture media was a custom modification of Minimum Essential Medium(Eagle) with Earle's salts (GibcoBRL) prepared without L-Arginine, without L-Glutamine and without phenol red and supplemented before use with 100 µM L-Arginine (Sigma), 2 mM L-glutamine, 1× HL-1 supplement (BioWhittaker), 50 mg/ml ascorbic acid (Sigma) and 150 pg/ml recombinant human IL-1β (RD Systems) to induce nitric oxide synthase. Compounds are then added in 10 µL aliquots and the explants incubated at 37 degrees C. with 5% CO$_2$ for 18–24 hours. The day old supernatant is then discarded and replaced with fresh culture media containing recombinant human IL-1β and compound and incubated for another 20–24 hours. This supernatant is analyzed for nitrite with a fluorometric assay (Misko et al, *Anal. Biochem.,* 214, 11–16, 1993). All samples are done in quadruplicate. The explants are weighed and the nitrite levels normalized to weight. Unstimulated controls are cultured in media in the absence of recombinant human IL-1β. IC$_{50}$ values are determined from plotting the percent inhibition of nitrite production at six different concentrations of inhibitor.

What is claimed:

1. A compound of Formula I

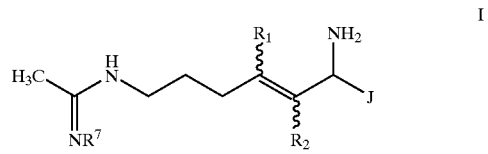

or a pharmaceutically acceptable salt thereof, wherein:

R$_1$ is selected from the group consisting of H, halo and alkyl which may be optionally substituted by one or more halo;

R₂ is selected from the group consisting of H, halo and alkyl which may be optionally substituted by one or more halo;

with the proviso that at least one of R₁ or R₂ is halo or alkyl substituted by one or more halo; and J is selected from the group consisting of carboxyl, hydroxyl; and NR₃R₄ wherein R₃ is selected from the group consisting of H, lower alkyl, lower alkylenyl and lower alkynyl; and R₄ is selected from the group consisting of H, and a heterocyclic ring in which at least one member of the ring is carbon and in which 1 to about 4 heteroatoms are independently selected from oxygen, nitrogen and sulfur and said heterocyclic ring may be optionally substituted with heteroarylamino, N-aryl-N-alkylamino, N-heteroarylamino-N-alkylamino, haloalkylthio, alkanoyloxy, alkoxy, heteroaralkoxy, cycloalkoxy, cycloalkenyloxy, hydroxy, amino, thio, nitro, lower alkylamino, alkylthio, alkylthioalkyl, arylamino, aralkylamino, arylthio, alkylsulfinyl, alkylsulfonyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkylenedioxy, haloalkylenedioxy, cycloalkyl, cycloalkenyl, lower cycloalkylalkyl, lower cycloalkenylalkyl, halo, haloalkyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, cyanoalkyl, dicyanoalkyl, carboxamidoalkyl, dicarboxamidoalkyl, cyanocarboalkoxyalkyl, carboalkoxyalkyl, dicarboalkoxyalkyl, cyanocycloalkyl, dicyanocycloalkyl, carboxamidocycloalkyl, dicarboxamidocycloalkyl, carboalkoxycyanocycloalkyl, carboalkoxycycloalkyl, dicarboalkoxycycloalkyl, formylalkyl, acylalkyl, dialkoxyphosphonoalkyl, diaralkoxyphosphonoalkyl, phosphonoalkyl, dialkoxyphosphonoalkoxy, diaralkoxyphosphonoalkoxy, phosphonoalkoxy, dialkoxyphosphonoalkylamino, diaralkoxyphosphonoalkylamino, phosphonoalkylamino, dialkoxyphosphonoalkyl, diaralkoxyphosphonoalkyl, guanidino, amidino, and acylamino.

2. The compound of claim 1 having a structure corresponding to Formula II:

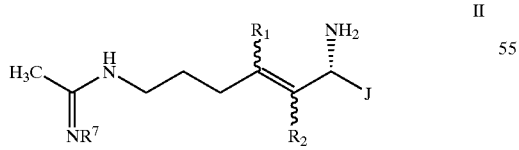

II or a pharmaceutically acceptable salt thereof, wherein:

R₁ is selected from the group consisting of H, halo and alkyl which may be optionally substituted by one or more halo;

R₂ is selected from the group consisting of H, halo and alkyl which may be optionally substituted by one or more halo;

with the proviso that at least one of R₁ or R₂ is halo or alkyl substituted by one or more halo; and J is selected from the group consisting of carboxyl, hydroxyl; and NR₃R₄ wherein R₃ is selected from the group consisting of H, lower alkyl, lower alkylenyl and lower alkynyl; and R₄ is selected from the group consisting of H, and a heterocyclic ring in which at least one member of the ring is carbon and in which 1 to about 4 heteroatoms are independently selected from oxygen, nitrogen and sulfur and said heterocyclic ring may be optionally substituted with heteroarylamino, N-aryl-N-alkylamino, N-heteroarylamino-N-alkylamino, haloalkylthio, alkanoyloxy, alkoxy, heteroaralkoxy, cycloalkoxy, cycloalkenyloxy, hydroxy, amino, thio, nitro, lower alkylamino, alkylthio, alkylthioalkyl, arylamino, aralkylamino, arylthio, alkylsulfinyl, alkylsulfonyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkylenedioxy, haloalkylenedioxy, cycloalkyl, cycloalkenyl, lower cycloalkylalkyl, lower cycloalkenylalkyl, halo, haloalkyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, cyanoalkyl, dicyanoalkyl, carboxamidoalkyl, dicarboxamidoalkyl, cyanocarboalkoxyalkyl, carboalkoxyalkyl, dicarboalkoxyalkyl, cyanocycloalkyl, dicyanocycloalkyl, carboxamidocycloalkyl, dicarboxamidocycloalkyl, carboalkoxycyanocycloalkyl, carboalkoxycycloalkyl, dicarboalkoxycycloalkyl, formylalkyl, acylalkyl, dialkoxyphosphonoalkyl, diaralkoxyphosphonoalkyl, phosphonoalkyl, dialkoxyphosphonoalkoxy, diaralkoxyphosphonoalkoxy, phosphonoalkoxy, dialkoxyphosphonoalkylamino, diaralkoxyphosphonoalkylamino, phosphonoalkylamino, dialkoxyphosphonoalkyl, diaralkoxyphosphonoalkyl, guanidino, amidino, and acylamino.

3. The compound of claim 1 having a structure corresponding to Formula III:

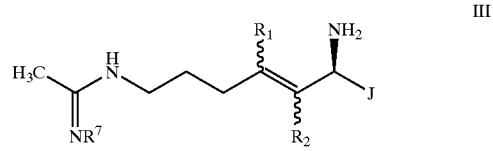

III or a pharmaceutically acceptable salt thereof, wherein:

R₁ is selected from the group consisting of H, halo and alkyl which may be optionally substituted by one or more halo;

R₂ is selected from the group consisting of H, halo and alkyl which may be optionally substituted by one or more halo;

with the proviso that at least one of R₁ or R₂ is halo or alkyl substituted by one or more halo; and J is selected from the group consisting of carboxyl, hydroxyl; and NR$_3$R$_4$ wherein R$_3$ is selected from the group consisting of H, lower alkyl, lower alkylenyl and lower alkynyl; and R$_4$ is selected from the group consisting of H, and a heterocyclic ring in which at least one member of the ring is carbon and in which 1 to about 4 heteroatoms are independently selected from oxygen, nitrogen and sulfur and said heterocyclic ring may be optionally substituted with heteroarylamino, N-aryl-N-alkylamino, N-heteroarylamino-N-alkylamino, haloalkylthio, alkanoyloxy, alkoxy, heteroaralkoxy, cycloalkoxy, cycloalkenyloxy, hydroxy, amino, thio, nitro, lower alkylamino, alkylthio, alkylthioalkyl, arylamino, aralkylamino, arylthio, alkylsulfinyl, alkylsulfonyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkylenedioxy, haloalkylenedioxy, cycloalkyl, cycloalkenyl, lower cycloalkylalkyl, lower cycloalkenylalkyl, halo, haloalkyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, cyanoalkyl, dicyanoalkyl, carboxamidoalkyl, dicarboxamidoalkyl, cyanocarboalkoxyalkyl, carboalkoxyalkyl, dicarboalkoxyalkyl, cyanocycloalkyl, dicyanocycloalkyl, carboxamidocycloalkyl, dicarboxamidocycloalkyl, carboalkoxycyanocycloalkyl, carboalkoxycycloalkyl, dicarboalkoxycycloalkyl, formylalkyl, acylalkyl, dialkoxyphosphonoalkyl, diaralkoxyphosphonoalkyl, phosphonoalkyl, dialkoxyphosphonoalkoxy, diaralkoxyphosphonoalkoxy, phosphonoalkoxy, dialkoxyphosphonoalkylamino, diaralkoxyphosphonoalkylamino, phosphonoalkylamino, dialkoxyphosphonoalkyl, diaralkoxyphosphonoalkyl, guanidino, amidino, and acylamino.

4. The compound of claim 1 wherein: R$_1$ is selected from the group consisting of H and C$_1$–C$_3$ alkyl which is optionally substituted by one or more halo, and R$_2$ is fluorine.

5. The compound of claim 1 wherein:
R$_1$ is H; and
R$_2$ is fluorine.

6. The compound of claim 1 wherein:
R$_1$ is halo; and
R$_2$ is halo.

7. The compound of claim 1 wherein:
R$_1$ is fluorine; and
R$_2$ is fluorine.

8. The compound of claim 1 wherein:
R$_1$ is fluorine; and
R$_2$ is H.

9. The compound of claim 1 wherein the compound is the S enantiomer.

10. The compound of claim 1 wherein the compound is the R enantiomer.

11. The compound of claim 1 wherein the compound is the E isomer.

12. The compound of claim 1 wherein the compound is the Z isomer.

13. A compound selected from the group consisting of:
(2S,3Z)-2-amino-4-fluoro-7-[(1-iminoethyl)amino]-3-heptenoic acid, dihydrochloride;
(2S,3E)-2-amino-4-fluoro-7-[(1-iminoethyl)amino]-3-heptenoic acid, dihydrochloride;
(3Z)-2-amino-3-fluoro-7-[(1-iminoethyl)amino]-3-heptenoic acid, dihydrochloride;
(3E)-2-amino-3-fluoro-7-[(1-iminoethyl)amino]-3-heptenoic acid, dihydrochloride;
(3E)-2-amino-3,4-difluoro-7-[(1-iminoethyl)amino]-3-heptenoic acid, dihydrochloride; and
(3Z)-2-amino-3,4-difluoro-7-[(1-iminoethyl)amino]-3-heptenoic acid, dihydrochloride.

14. A pharmaceutical composition comprising a compound of claim 1 and a pharmaceutically acceptable carrier.

15. A method of inhibiting nitric oxide synthesis in a human subject in need of such inhibition by administering a therapeutically effective amount of a compound of claim 1.

16. A method of selectively inhibiting nitric oxide produced by inducible nitric oxide synthase over nitric oxide produced by the constitutive forms of nitric oxide synthase in a human subject in need of such inhibition by administering a therapeutically an effective amount of a compound of claim 1.

17. A method of lowering nitric oxide levels in a human subject in need of such by administering a therapeutically effective amount of a compound of claim 1.

18. A method of lowering nitric oxide levels in a human subject in need of such by administering a therapeutically effective amount of a pharmaceutical composition comprising a compound of claim 1.

19. The pharmaceutically-acceptable salt of claim 1 having at least one anionic counterion.

20. The pharmaceutically-acceptable salt of claim 19 wherein the anionic counterion is selected from the group consisting of a halide, a carboxylate, a sulfonate, a sulfate, a phosphate, a phosphonate, a resin-bound anion, and a nitrate.

21. The pharmaceutically-acceptable salt of claim 20 wherein the anionic counterion is a halide.

22. The pharmaceutically-acceptable salt of claim 21 wherein the halide is chloride.

23. The pharmaceutically-acceptable salt of claim 20 wherein the anionic counterion is a carboxylate.

24. The pharmaceutically-acceptable salt of claim 23 wherein the carboxylate is selected from the group consisting of formate, acetate, propionate, trifluoroacetate, succinate, salicylate, DL-aspartate, D-aspartate, L-aspartate, DL-glutamate, D-glutamate, L-glutamate, glycerate, succinate, steric, DL-tartarate, D-tartarate, L-tartarate, (±)-mandelate, (R)-(−)-mandelate, (S)-(+)-mandelate, citrate, mucate, maleate, malonate, benzoate, DL-malate, D-malate, L-malate, hemi-malate, 1-adamantaneacetate, 1-adamantanecarboxylate, flavianate, sulfonoacetate, (±)-lactate, L-(+)-lactate, D-(−)-lactate, pamoate, D-alpha-galacturonate, glycerate, DL-cystate, D-cystate, L-cystate, DL-homocystate, D-homocystate, L-homocystate, DL-cysteate, D-cysteate, L-cysteate, (4S)-hydroxy-L-proline, cyclopropane-1,1-dicarboxylate, 2,2-dimethylmalonate, squarate, tyrosine anion, proline anion, fumarate, 1-hydroxy-2-naphthoate, phosphonoacetate, carbonate, bicarbonate, 3-phosphonopropionate, DL-pyroglutamate, D-pyroglutamate, and L-pyroglutamate.

25. The pharmaceutically-acceptable salt of claim 20 wherein the anionic counterion is a sulfonate.

26. The pharmaceutically-acceptable salt of claim 25 wherein the sulfonate is selected from the group consisting of methanesulfonate, toluenesulfonate, benzenesulfonate, trifluoromethylsulfonate, ethanesulfonate, (±)-camphorsulfonate, naphthalenesulfonate, 1R-(−)-camphorsulfonate, 1S-(+)-camphorsulfonate, 2-mesitylenesulfonate, 1,5-naphthalenedisulfonate, 1,2-ethanedisulfonate, 1,3-propanedisulfonate, 3-(N-morpholino)propane sulfonate, biphenylsulfonate, isethionate, and 1-hydroxy-2-naphthalenesulfonate.

27. The pharmaceutically-acceptable salt of claim 20 wherein the anionic counterion is a sulfate.

28. The pharmaceutically-acceptable salt of claim 27 wherein the sulfate is selected from the group consisting of sulfate, monopotassium sulfate, monosodium sulfate, and hydrogen sulfate.

29. The pharmaceutically-acceptable salt of claim 20 wherein the anionic counterion is a sulfamate.

30. The pharmaceutically-acceptable salt of claim 20 wherein the anionic counterion is a phosphate.

31. The pharmaceutically-acceptable salt of claim 30 wherein the phosphate is selected from the group consisting of phosphate, dihydrogen phosphate, potassium hydrogen phosphate, dipotassium phosphate, potassium phosphate, sodium hydrogen phosphate, disodium phosphate, sodium phosphate, calcium phosphate, and hexafluorophosphate.

32. The pharmaceutically-acceptable salt of claim 20 wherein the anionic counterion is a phosphonate.

33. The pharmaceutically-acceptable salt of claim 32 wherein the phosphonate is selected from the group consisting of vinylphosphonate, 2-carboxyethylphosphonate and phenylphosphonate.

34. The pharmaceutically-acceptable salt of claim 20 wherein the anionic counterion is a resin-bound anion.

35. The pharmaceutically-acceptable salt of claim 34 wherein the resin-bound anion is selected from the group consisting of a resin comprising polyacrylate and a resin comprising sulfonated poly(styrene divinylbenzene).

36. The pharmaceutically-acceptable salt of claim 20 wherein the anionic counterion is nitrate.

37. The pharmaceutically-acceptable salt of claim 19 wherein the anion is selected from the group consisting of DL-ascorbate, D-ascorbate, and L-ascorbate.

38. The pharmaceutically-acceptable salt of claim 1 having at least one cationic counterion.

39. The pharmaceutically-acceptable salt of claim 38 wherein the cationic counterion is selected from the group consisting of an ammonium cation, a alkali metal cation, an alkaline earth metal cation, a transition metal cation, and a resin-bound cation.

40. The pharmaceutically-acceptable salt of claim 39 wherein the cationic counterion is an ammonium cation.

41. The pharmaceutically-acceptable salt of claim 40 wherein the ammonium cation is selected from the group consisting of ammonium, methyl ammonium, dimethylammonium, trimethylammonium, tetramethylammonium, ethanolammonium, dicyclohexylammonium, guanidinium, and ethylenediammonium cation.

42. The pharmaceutically-acceptable salt of claim 39 wherein the cationic counterion is an alkali metal cation.

43. The pharmaceutically-acceptable salt of claim 42 wherein the alkali metal cation is selected from the group consisting of lithium cation, sodium cation, potassium cation, and cesium cation.

44. The pharmaceutically-acceptable salt of claim 39 wherein the cationic counterion is an alkaline earth metal cation.

45. The pharmaceutically-acceptable salt of claim 44 wherein the alkaline earth metal cation is selected from the group consisting of beryllium cation, magnesium cation, and calcium cation.

46. The pharmaceutically-acceptable salt of claim 39 wherein the cationic counterion is a transition metal cation.

47. The pharmaceutically-acceptable salt of claim 46 wherein the transition metal cation is a zinc cation.

48. The pharmaceutically-acceptable salt of claim 39 wherein the cationic counterion is a resin-bound cation.

49. The pharmaceutically-acceptable salt of claim 48 wherein the resin-bound cation is a cationically functionalized poly(styrene divinylbenzene) resin.

50. The pharmaceutically-acceptable salt of claim 49 wherein the resin-bound cation is an aminated poly(styrene divinylbenzene) resin.

51. The pharmaceutically-acceptable salt of claim 48 wherein the resin-bound cation is a cationically functionalized polyacrylic resin.

52. The pharmaceutically-acceptable salt of claim 48 wherein the resin-bound cation is an aminated polyacrylic resin.

53. A compound having the Formula IV:

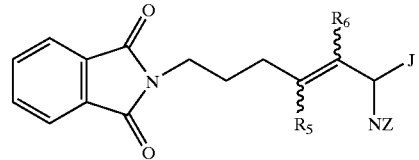

IV wherein
$R^5$ is selected from the group consisting of H, F, and methyl;
$R^6$ is selected from the group consisting of H, F, and methyl;
with the proviso that either $R^5$ or $R^6$ must be F;
J is selected from the group consisting of H, hydroxy, alkoxy; and $NR^3R^4$ where $R^3$ is selected from the group consisting of H, lower alkyl, lower alkylenyl and lower alkynyl; and $R^4$ is selected from the group consisting of H, and a heterocyclic ring in which at least one member of the ring is carbon and in which 1 to about 4 heteroatoms are independently selected from oxygen, nitrogen and sulfur and said heterocyclic ring may be optionally substituted with heteroarylamino, N-aryl-N-alkylamino, N-heteroarylamino-N-alkylamino, haloalkylthio, alkanoyloxy, alkoxy, heteroaralkoxy, cycloalkoxy, cycloalkenyloxy, hydroxy, amino, thio, nitro, lower alkylamino, alkylthio, alkylthioalkyl, arylamino, aralkylamino, arylthio, alkylsulfinyl, alkylsulfonyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkylenedioxy, haloalkylenedioxy, cycloalkyl, cycloalkenyl, lower cycloalkylalkyl, lower cycloalkenylalkyl, halo, haloalkyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, cyanoalkyl, dicyanoalkyl, carboxamidoalkyl, dicarboxamidoalkyl, cyanocarboalkoxyalkyl, carboalkoxyalkyl, dicarboalkoxyalkyl, cyanocycloalkyl, dicyanocycloalkyl, carboxamidocycloalkyl, dicarboxamidocycloalkyl, carboalkoxycyanocycloalkyl, carboalkoxycycloalkyl, dicarboalkoxycycloalkyl, formylalkyl, acylalkyl, dialkoxyphosphonoalkyl, diaralkoxyphosphonoalkyl, phosphonoalkyl, dialkoxyphosphonoalkoxy, diaralkoxyphosphonoalkoxy, phosphonoalkoxy, dialkoxyphosphonoalkylamino, diaralkoxyphosphonoalkylamino, phosphonoalkylamino, dialkoxyphosphonoalkyl, diaralkoxyphosphonoalkyl, guanidino, amidino, and acylamino;

Q is H, or an appropriate nitrogen protecting moiety.

54. A method of treating an inflammation related condition in a human subject in need of such treatment or prevention comprising:

administering a treatment effective amount of a compound of formula I

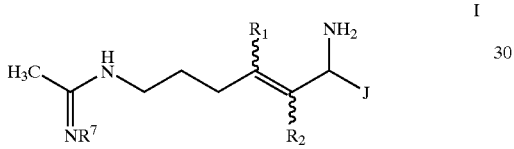

or a pharmaceutically acceptable salt thereof, wherein:
$R^1$ is selected from the group consisting of H, halo and alkyl which is optionally substituted by one or more halo;
$R^2$ is selected from the group consisting of H, halo and alkyl which is optionally substituted by one or more halo;
with the proviso that at least one of $R_1$ or $R_2$ is halo or alkyl substituted by one or more halo; $R^1$ is selected from the group consisting of H, halo and alkyl which is optionally substituted by one or more halo;
$R^2$ is selected from the group consisting of H, halo and alkyl which is optionally substituted by one or more halo;
with the proviso that at least one of $R^1$ or $R^2$ contains a halo;
$R^7$ is selected from the group consisting of H and hydroxy; and
J is selected from the group consisting of hydroxy, carboxyl, carboalkoxy, and C(O)NR3R4 wherein;
$R^3$ is selected from the group consisting of H, lower alkyl, lower alkylenyl and lower alkynyl; and
$R^4$ is selected from the group consisting of H, and a heterocyclic ring in which at least one member of the ring is carbon and in which 1 to about 4 heteroatoms are independently selected from oxygen, nitrogen and sulfur; and said heterocyclic ring is optionally substituted with a moiety selected from the group consisting of heteroarylamino, N-aryl-N-alkylamino, N-heteroarylamino-N-alkylamino, haloalkylthio, alkanoyloxy, alkoxy, heteroaralkoxy, cycloalkoxy, cycloalkenyloxy, hydroxy, amino, thio, nitro, alkylamino, dialkyamino, alkylthio, alkylthioalkyl, arylamino, aralkylamino, arylthio, alkylsulfinyl, alkylsulfonyl, alkylsulfonamido, alkylaminosulfonyl, aminosulfonyl, monoalkyl aminosulfonyl, dialkyl aminosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkylenedioxy, haloalkylenedioxy, carboxyl, alkoxycarboxyl, cycloalkyl, cycloalkenyl, lower cycloalkylalkyl, lower cycloalkenylalkyl, halo, haloalkyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, cyanoalkyl, dicyanoalkyl, carboxamidoalkyl, dicarboxamidoalkyl, cyanocarboalkoxyalkyl, carboxyalkoxyalkyl, dicarboxyalkoxyalkyl, cyanocycloalkyl, dicyanocycloalkyl, carboxamidocycloalkyl, dicarboxamidocycloalkyl, carboalkoxycyanocycloalkyl, carboalkoxycycloalkyl, dicarboalkoxycycloalkyl, formylalkyl, acylalkyl, dialkoxyphosphonoalkyl, diaralkoxyphosphonoalkyl, phosphonoalkyl, dialkoxyphosphonoalkoxy, diaralkoxyphosphonoalkoxy, phosphonoalkoxy, dialkoxyphosphonoalkylamino, diaralkoxyphosphonoalkylamino, phosphonoalkylamino, dialkoxyphosphonoalkyl, diaralkoxyphosphonoalkyl, guanidino, amidino, and acylamino to a human subject in need of such treatment.

55. The method of claim 54 wherein said inflammation related condition is an arthritis condition.

56. The method of claim 55 wherein said arthritis condition is osteoarthritis.

57. The method of claim 55 wherein said arthritis condition is rhumatoid arthritis.

58. The method of claim 54 wherein said inflammation related condition is post-operative inflammation.

59. The method of claim 58 wherein said post-operative inflammation is associated with ophthalmic surgery.

60. The method of claim 59 wherein said ophthalmic surgery is cataract surgery.

61. The method of claim 54 wherein said inflammation related condition is associated with an infection.

62. The method of 61 wherein said infection is sepsis.

63. The method of claim 59 wherein said infection is caused by a virus.

64. The method of claim 54 wherein said inflammation related condition is inflammatory bowel syndrome.

65. The method of claim 54 wherein said inflammatory related condition is caused by injury.

66. The method of claim 54 wherein said inflammatory related condition is pulmonary inflammation.

67. The method of claim 66 wherein said pulmonary inflammation is caused by cystic fibrosis.

68. A method of treating a malignant neoplasia in a human subject in need of such treatment comprising:

administering a treatment or prevention effective amount of a compound of formula I

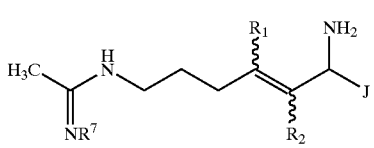

or a pharmaceutically acceptable salt thereof, wherein:
R$^1$ is selected from the group consisting of H, halo and alkyl which is optionally substituted by one or more halo;
R$^2$ is selected from the group consisting of H, halo and alkyl which is optionally substituted by one or more halo;
with the proviso that at least one of R$_1$ or R$_2$ R$_2$ is halo or alkyl substituted by one or more halo; R$^1$ is selected from the group consisting of H, halo and alkyl which is optionally substituted by one or more halo;
R$^2$ is selected from the group consisting of H, halo and alkyl which is optionally substituted by one or more halo;
with the proviso that at least one of R$^1$ or R$^2$ is halo or alkyl substituted by one or more halo;
R$^7$ is selected from the group consisting of H and hydroxy; and
J is selected from the group consisting of hydroxy, carboxyl, carboalkoxy, and C(O)NR3R4 wherein;
R$^3$ is selected from the group consisting of H, lower alkyl, lower alkylenyl and lower alkynyl; and
R$^4$ is selected from the group consisting of H, and a heterocyclic ring in which at least one member of the ring is carbon and in which 1 to about 4 heteroatoms are independently selected from oxygen, nitrogen and sulfur; and said heterocyclic ring is optionally substituted with a moiety selected from the group consisting of heteroarylamino, N-aryl-N-alkylamino, N-heteroarylamino-N-alkylamino, haloalkylthio, alkanoyloxy, alkoxy, heteroaralkoxy, cycloalkoxy, cycloalkenyloxy, hydroxy, amino, thio, nitro, alkylamino, dialkyamino, alkylthio, alkylthioalkyl, arylamino, aralkylamino, arylthio, alkylsulfinyl, alkylsulfonyl, alkylsulfonamido, alkylaminosulfonyl, aminosulfonyl, monoalkyl aminosulfonyl, dialkyl aminosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkylenedioxy, haloalkylenedioxy, carboxyl, alkoxycarboxyl, cycloalkyl, cycloalkenyl, lower cycloalkylalkyl, lower cycloalkenylalkyl, halo, haloalkyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, cyanoalkyl, dicyanoalkyl, carboxamidoalkyl, dicarboxamidoalkyl, cyanocarboalkoxyalkyl, carboxyalkoxyalkyl, dicarboxyalkoxyalkyl, cyanocycloalkyl, dicyanocycloalkyl, carboxamidocycloalkyl, dicarboxamidocycloalkyl, carboalkoxycyanocycloalkyl, carboalkoxycycloalkyl, dicarboalkoxycycloalkyl, formylalkyl, acylalkyl, dialkoxyphosphonoalkyl, diaralkoxyphosphonoalkyl, phosphonoalkyl, dialkoxyphosphonoalkoxy, diaralkoxyphosphonoalkoxy, phosphonoalkoxy, dialkoxyphosphonoalkylamino, diaralkoxyphosphonoalkylamino, phosphonoalkylamino, dialkoxyphosphonoalkyl, diaralkoxyphosphonoalkyl, guanidino, amidino, and acylamino to a human subject in need of such treatment.

69. The method of claim 68 wherein said cancer is an epithelial cell-derived neoplasia.
70. The method of claim 69 wherein said epithelial cell-derived neoplasia is a gastrointestinal cancer.
71. The method of claim 70 wherein said epithelial cell-derived neoplasia is colon cancer.
72. The method of claim 70 wherein said epithelial cell derived neoplasia is lung cancer.
73. The method of claim 69 wherein said epithelial cell derived neoplasia is prostate cancer.
74. The method of claim 69 wherein said epithelial cell derived neoplasia is cervical cancer.
75. The method of claim 69 wherein said epithelial cell derived neoplasia is breast cancer.
76. The method of claim 68 wherein said malignant neoplasia is mesenchymal tissue derived.
77. A method of treating addiction in a human subject in need of such treatment comprising:
administering a treatment effective amount of a compound of formula I

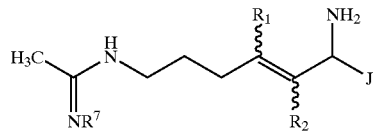

or a pharmaceutically acceptable salt thereof, wherein:
R$^1$ is selected from the group consisting of H, halo and alkyl which is optionally substituted by one or more halo;
R$^2$ is selected from the group consisting of H, halo and alkyl which is optionally substituted by one or more halo;
with the proviso that at least one of R$_1$ or R$_2$ is halo or alkyl substituted by one or more halo; R$^1$ is selected from the group consisting of H, halo and alkyl which is optionally substituted by one or more halo;
R$^2$ is selected from the group consisting of H, halo and alkyl which is optionally substituted by one or more halo;
with the proviso that at least one of R$^1$ or R$^2$ contains a halo;
R$^7$ is selected from the group consisting of H and hydroxy; and
J is selected from the group consisting of hydroxy, carboxyl, carboalkoxy, and C(O)NR3R4 wherein;
R$^3$ is selected from the group consisting of H, lower alkyl, lower alkylenyl and lower alkynyl; and $R^4$ is selected from the group consisting of H, and a heterocyclic ring in which at least one member of the ring is carbon and in which 1 to about 4 heteroatoms are independently selected from oxygen, nitrogen and sulfur; and said heterocyclic ring is optionally substituted with a moiety selected from the group consisting of heteroarylamino, N-aryl-N-alkylamino, N-heteroarylamino-N-alkylamino, haloalkylthio, alkanoyloxy, alkoxy, heteroaralkoxy, cycloalkoxy, cycloalkenyloxy, hydroxy, amino, thio, nitro, alkylamino, dialkyamino, alkylthio, alkylthioalkyl, arylamino, aralkylamino, arylthio, alkylsulfinyl, alkylsulfonyl, alkylsulfonamido, alkylaminosulfonyl, aminosulfonyl, monoalkyl aminosulfonyl, dialkyl aminosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, alkanoyl, alkenoyl, aroyl, heteroaroyl, aralkanoyl, heteroaralkanoyl, haloalkanoyl, alkyl, alkenyl, alkynyl, alkylenedioxy, haloalkylenedioxy, carboxyl, alkoxycarboxyl, cycloalkyl, cycloalkenyl, lower cycloalkylalkyl, lower cycloalkenylalkyl, halo, haloalkyl, haloalkoxy, hydroxyhaloalkyl, hydroxyaralkyl, hydroxyalkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, heteroarylalkenyl, cyanoalkyl, dicyanoalkyl, carboxamidoalkyl, dicarboxamidoalkyl, cyanocarboalkoxyalkyl, carboxyalkoxyalkyl, dicarboxyalkoxyalkyl, cyanocycloalkyl, dicyanocycloalkyl, carboxamidocycloalkyl, dicarboxamidocycloalkyl, carboalkoxycyanocycloalkyl, carboalkoxycycloalkyl, dicarboalkoxycycloalkyl, formylalkyl, acylalkyl, dialkoxyphosphonoalkyl, diaralkoxyphosphonoalkyl, phosphonoalkyl, dialkoxyphosphonoalkoxy, diaralkoxyphosphonoalkoxy, phosphonoalkoxy, dialkoxyphosphonoalkylamino, diaralkoxyphosphonoalkylamino, phosphonoalkylamino, dialkoxyphosphonoalkyl, diaralkoxyphosphonoalkyl, guanidino, amidino, and acylamino, to a human subject in need of such treatment.

\* \* \* \* \*